US006894161B2

(12) United States Patent
Desjardins et al.

(10) Patent No.: US 6,894,161 B2
(45) Date of Patent: May 17, 2005

(54) METHODS AND COMPOSITIONS FOR PHOTO-CROSS LINKING PHOTOACTIVE COMPOUNDS TO TARGET TISSUE

(75) Inventors: Angela M. Desjardins, London (CA); David H. Dolphin, Vancouver (CA); Ethan D. Sternberg, Vancouver (CA)

(73) Assignee: The University of British Columbia, Vancouver (CA)

( * ) Notice: Subject to any disclaimer, the term of this patent is extended or adjusted under 35 U.S.C. 154(b) by 284 days.

(21) Appl. No.: 10/109,141

(22) Filed: Mar. 27, 2002

(65) Prior Publication Data

US 2003/0013696 A1 Jan. 16, 2003

Related U.S. Application Data

(60) Provisional application No. 60/279,233, filed on Mar. 27, 2001.

(51) Int. Cl.$^7$ ...................... C09B 47/04; A61K 31/555; A61K 31/685
(52) U.S. Cl. ...................... 540/125; 540/123; 540/128; 540/140; 540/145; 514/43; 514/63; 514/150; 514/151; 514/185; 514/191; 514/410; 514/183; 604/20; 604/204; 604/157.81
(58) Field of Search ............................ 540/123, 125, 540/128, 140, 145; 514/43, 63, 150, 151, 185, 191, 410; 604/20; 204/157.81

(56) References Cited

U.S. PATENT DOCUMENTS

| 5,459,159 A | | 10/1995 | Pandey et al. ............... 514/410 |
| 5,484,778 A | * | 1/1996 | Kenney et al. ................ 514/63 |
| 5,829,448 A | * | 11/1998 | Fisher et al. ................ 128/898 |
| 6,121,027 A | * | 9/2000 | Clapper et al. ............. 435/180 |

OTHER PUBLICATIONS

Adam et al. "The Synthesis of Unusual Organic Molecules from Azoalkanes" Angew. Chem. Int. Ed. Engl. 19:762–779 (1980).
Black. "The Preparation and Reactions of Diazomethane" Aldrichimica Acta 16:3–10 (1983).
Boldyrev and Schleyer. "Ab Initio Investigation of the Structures and Stabilities of $CH_2N_2$, $CHFN_2$, and $CF_2N_2$ Isomers: Isomers: Important Consequences of MP2 Optimizations" Comput. Chem. 13(9):1066–1078 (1992).
Boyd et al. "Photoaffinity Labeling the Substance P Receptor Using a Derivative of Substance P Containing p-Benzoylphenylalanine" Biochemistry30:336–342 (1991).
Brunner et al. "3–Trifluoromethyl–3–phenyldiazirine" J. Biol. Chem. 255:3313–3318 (1980).
Carey et al. *Advanced Organic Chemistry*; (3$^{rd}$ Ed.) Plenum Press: New York; p. 635 (1990).
Dorman et al. "Benzophenone Photophores in Biochemistry" Biochemistry 33(19):5661–5673 (1994).

Durr et al. "Triplet States from Azides" Top. Curr. Chem. 66:89–114 (1976).
Ehret–Sabatier et al. "Photosuicide Labeling" NATO ASI Ser., Ser. C; Photochem Probes Biochem. 272:107–122 (1989).
Engel et al. "Photochemical Decomposition and Isomerization of Aliphatic Azo Compounds" J. Pure Appl. Chem. 52:2621–2632 (1980).
Fedan et al. "Photoaffinity Labels as Pharmacological Tools" Biochem. Pharmacol. 33(8):1167–1180 (1984).
Fleet et al. "Affinity Labelling of Antibodies with Aryl Nitrene as Reactive Group" Nature 224:511–.
Fleming. "Chemical Reagents in Photoaffinity Labeling" Tetrahedron 51(46):12479–12520 (1995).
Griffiths et al. "Preparation and Use of Tetra–n butylammonium Per–ruthenate (TBAP Reagent) and Tetra–n–propylammonium Per–ruthenate (TPAP Reagent) I as New Catalytic Oxidants for Alcohols" J. Chem. Soc., Chem. Commun. 1625 (1988).
Hiberty et al. "Organic Transition States. 6. Thermal Decomposition of 1–Pyrazolines" J. Am. Chem. Soc. 101(10):2538–2543 (1979).
Li et al. "Application of Ruppert's Reagent in Preparaing Novel Perfluorinated Porphyrins, Chlorins and Bacteriochlorins" J. Chem. Soc. Perkin Trans 1:1785–1787 (1999).
Mettath et al. "Synthesis and Spectroscopic Properties of Novel Benzochlorins Derived from Chlorophyll a" J. Org. Chem. 63:1646–1656 (1998).
Meier et al. "Thermal and Photochemical Cycloelimination of Nitrogen" Angew. Chem. Int. Ed. Engl. 16:835–851 (1977).
Newton et al. "Synthesis of Stable Prostacyclin Analogues from 2,3–Distributed Bicyclo[3.2.0] Heptan–6–Ones" J. Chem. Soc. Perkin Trans. 1:823–830 (1982).
Pascual et al. "Photoaffinity Labeling of Thyroid Hormone Nuclear Receptors in Intact Cells" J. Biol. Chem. 257:9640–9647 (1982).
Pizey. "Raney Nickel (Ra/Ni)" In *Synthetic Reagents*; Halstead: New York; 2:175–311 (1974).
Ponomarev et al. "Porphyrins. Synthesis and Properties of 1–Substituted Derivatives of 5, 10, 15, 20– Tetraphenylporphyrin" Chemistry of Heterocyclic Compounds 18:50–55 (1982).
Potter. "PT Dosimetry and Response" In Proceedings of SPIE 1065:88–99 (1989).

(Continued)

*Primary Examiner*—Shailendra Kumar
(74) *Attorney, Agent, or Firm*—Morrison & Foerster LLP

(57) ABSTRACT

The present invention discloses novel photoactive compounds that may be crosslinked to target substrates. Methods for the preparation and use of the compounds, as well as compositions comprising them, are also disclosed.

8 Claims, 8 Drawing Sheets

OTHER PUBLICATIONS

Prakash et al. "Fluoride–Induced Trifluoromethylation of Carbonyl Compounds with Trifluoromethyltrimethylsilane (TMS–$CF_3$). A Trifluoromethide Equivalent" J. Am. Chem. Soc. 111:393–395 (1989).

Rao et al. "3–(p–Azidobenzamido)taxol Photolabels the N–terminal 31 Amino Acids of β–Tubulin" J. Biol. Chem. 269(5):3132–3134 (1994).

Rau. "Spectroscopic Properties of Organic Azo Compounds" Angew. Chem. Inct. Ed. Engl. 12(3):224–235(1973).

Schrock et al. "Photochemistry of Phenyl Azide: Chemical Properties of the Transient Intermediates" J. Am. Chem. Soc. 106:5228–5234 (1984).

Schuster et al. "Photoaffinity Labeling" Photochem Photobiol. 49(6):785–804 (1989).

Schuster et al. "Photochemistry of Phenyl Azide" Adv. Photochem. 17:69–143 (1992).

Shih et al. "A Carbene–Yielding Amino Acid for Incorporation into Peptide Photoaffinity Reagents" Analytical Biochemistry 144:132–141 (1985).

Swindell et al. "Characterization of Two Taxol Photoaffinity Analogues Bearing Azide and Benzophenone–Related Photoreactive Substituents in the A–Ring Side Chain" J. Med. Chem. 37:1446–1449 (1994).

Tschirret–Guth et al. "Trifluoromethyldiazirinylphenyldiazenes: New Hemoprotein Active–Site Probes" J. Am. Chem. Soc. 4731–4737 (1999).

Wiberg et al. "Preparation and Diels–Alder Reactions of the [n](1,4)Napthalenophanes. Isolation of a Paddlane Derivative Containing the Tricyclo[$14.2.2.2^{1,6}$]docosane Ring System" J. Am. Chem. Soc. 101(22):6660–6666 (1979).

Wijesekera et al. "Synthetic Aspects of Porphyrin and Metalloporphyrin Chemistry" *In Metallopophyrins in Catalytic Oxidations* (Sheldon, Ed.) New York pp. 193–239 (1994).

* cited by examiner

1A

1B

1C

1D

2A

2B

2A

2D

2E

2F

3A

3B

3C

3D

METHODS AND COMPOSITIONS FOR PHOTO-CROSS LINKING PHOTOACTIVE COMPOUNDS TO TARGET TISSUE

CROSS-REFERENCE TO RELATED APPLICATIONS

This application claims benefit of priority to U.S. Provisional Application 60/279,233, filed Mar. 27, 2001, which is hereby incorporated in its entirety as if fully set forth.

TECHNICAL FIELD

The invention is directed to photosensitive compounds, and compositions containing them, that are useful in photodynamic therapy (PDT) and adapted with a functional moiety that is capable of being cross-linked to target molecules or tissues upon exposure to light. Methods of preparing such compounds and using them for PDT are also provided.

BACKGROUND ART

Photodynamic therapy is a minimally invasive two-step medical procedure that uses light-activated agents called photosensitizers to treat a range of diseases involving rapid cell growth, such as cancerous tumors or abnormal blood vessels. In one instance, a photosensitizer is administered and, once in the bloodstream, associates with lipoproteins. Rapidly dividing cells require more lipoproteins than normal cells, thus a higher concentration of the drug accumulates in these tissues. The photosensitizer is then activated by exposure to light containing a wavelength which activates the photosensitizer. Once activated, the photosensitizer converts oxygen found in the cells into highly energized singlet oxygen. Singlet oxygen can react with subcellular components such as proteins and lipids, which disrupts normal cellular function and results in killing the cells. Lasers and fiber optics are used to deliver the activating light.

Photolysis of a photoactivatable moiety generates an intermediate which reacts to result in a crosslink to another molecule. Several classes of reactive intermediates have been exploited in photoaffinity labeling; the predominant ones being nitrenes, radicals and carbenes. Nitrenes stemming from aryl azides have been studied extensively and appear throughout the literature. Scheme A below shows that irradiation produces a singlet nitrene that intersystem crosses to the ground state triplet (at low temperatures, some chemistry from the singlet is observed to form 2). The triplet nitrene is expected to behave like a diradical, and is hoped to effect useful binding by hydrogen abstraction then radical coupling (Schuster, G. B.; Platz, M. S. Adv. Photochem. 1992, 17, 69–143).

Scheme A
Photochemistry of nitrenes

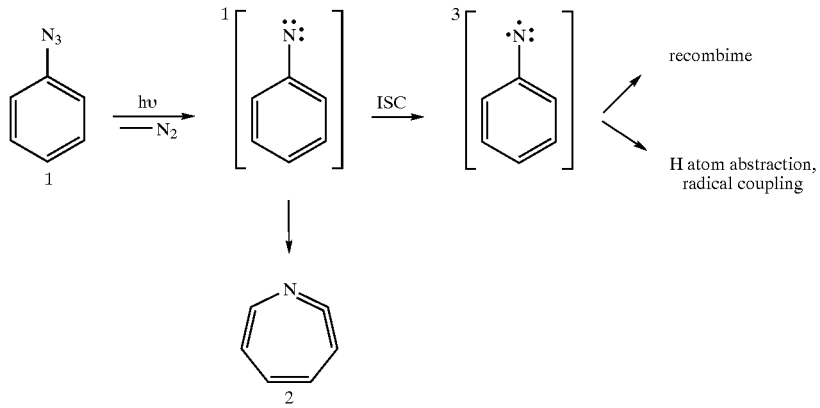

A representative example of the use of azides in photoaffinity labeling is found in the work of Swindell et. al. (Swindell, C. S.; Heerding, J. M.; Krauss, N. E. J. Med. Chem. 1994, 37, 1446–1449). A photoaffinity taxol analogue that bears an azide photoreactive moiety in the A-ring side chain of taxol was used to label the N-terminal domain of β-tubulin with specificity.

Radical intermediates are ideally suited for photoaffinity labeling. They are known to abstract hydrogen atoms from virtually any site, are more reactive with C—H bonds than are nitrenes and have less propensity for intramolecular rearrangements than carbenes. Examples of radical generating photoprobes include benzophenone (Dorman, G.; Prestwich, G. D. Biochemistry 1994, 33, 5661–5673), enones (Boyd, N. D.; Cerpa, R.; Kaiser, E. T.; Leeman, S. E.; White, C. F. Biochemistry 1991, 30, 336–342), and various diazo/diazonium compounds whereby loss of $N_2$ results in the reactive intermediate (Ehret-Sabatier, L.; Kieffer, B.; Goeldner, M. Hirth, C. NATO ASI Ser., Ser. C; Photochem. Probes Biochem. 1989, 272, 107–122).

Diazirines are capable of generating carbenes as reactive intermediates. Most of the recent work with diazirines exploits the photochemical reactivity of the trifluoroethyldiazirinephenyl group (Brunner, J.; Senn, H.; Richards, F. M. J. Biol. Chem. 1980, 255, 3313–3318). Irradiation of a substituted diazirine (4) (Scheme B below) has been shown to give carbene (5) and the corresponding diazo compound (6).

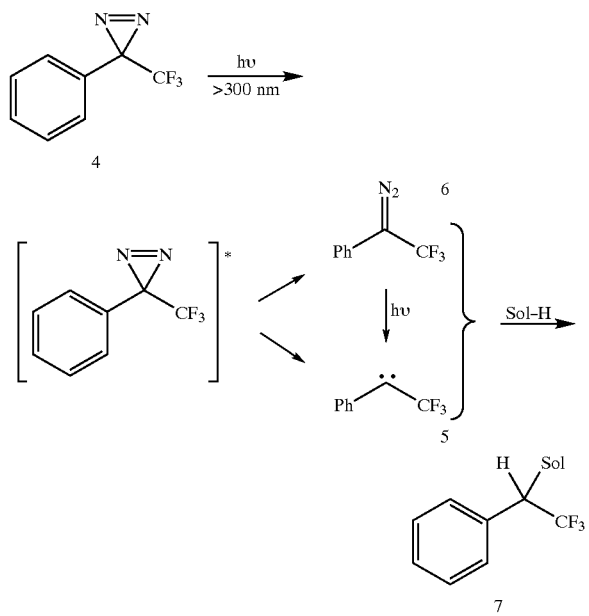

Scheme B
Photochemistry of diazirines

Carbenes have the ability to insert into carbon-hydrogen bonds (Sol-H) to yield products like 7. The diazirine unit is small, non-bulky, and lipophillic. It has a chromophore that extends significantly into the 300 nm range. Many applications of photo cross-linking have been reported for this functionality. Shih et al. (*Anal. Biochem.* 1985, 144, 132–141) reported the synthesis, radioisotopic labeling, and resolution of a phenylalanine analog, 3-[p-[3-(trifluoromethyl)-3H-dizirin-3-yl]phenylalanine (8), containing the 3-(trifluoromethyl)-3H-diazirinyl group. Like all diazirines, 8 absorbs in the near UV ($\lambda_{max}$ 350; $\epsilon$ 265).

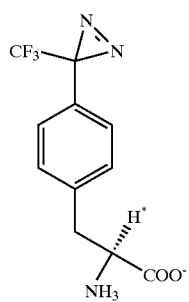

Photodynamic therapy is a relatively safe treatment, because without exposure to light, the drug has no effect. Furthermore, the drug accumulates primarily in diseased cells as described above, thus upon irradiation the effects on surrounding healthy tissue are minimized.

Effective photosensitizers include porphyrogenic compounds with strong absorption coefficients at wavelengths in the red region of the electromagnetic spectrum. At this wavelength, human tissue is the most transparent to light, and allows efficient excitation of the photosensitizer drug, causing the most phototoxic effect (Potter, W. R. In Proceedings of SPIE 1989, 1065, 88). Unfortunately, red light is present in ambient daylight, and patients who undergo PDT experience varying degrees of skin photosensitivity resulting from residual photosensitizer in healthy tissue. Depending upon the rate of elimination of a particular photosensitizer, this period of skin photosensitivity can range from a day or two to several weeks. This side effect of PDT has prompted an exploration of possible structural modifications of the photosensitizers, and new ways of using visible light for their photoactivation.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

DISCLOSURE OF THE INVENTION

The present invention is based in part upon the unexpected discovery of the ability to use long wavelength, and thus lower energy, light to photoactivate chemical moieties for crosslinking (i.e. photocrosslinking). Historically, photocrosslinking has been applied as part of photoaffinity labeling to locate active sites and binding sites in enzyme-substrate complexes. As a result of covalent bonding between substrates and a variety of cellular components, enzymes, membranes, protein structures, neural receptors, and RNA or DNA structures have been successfully labeled (see Fedan, J. S.; Hogaboom, G. K.; O'Donnell, J. P. Biochem. Pharmacol. 1984, 33, 1167–1180; Rao, S.; Krauss, N. E.; Heerding, J. M.; Swindell, I. R.; Ringel, I.; Orr, G. A.; Horwitz, S. B. J. Biol. Chem. 1994, 269, 3132–3134; Schuster, D. I.; Probst, W. C.; Ehrlich, G. K.; Singh, G. Photochem. Photobiol. 1989, 49, 785–804; and Morrison, H.; Ed. Bioorganic Photochemistry, Vol. 1, Photochemistry and Nucleic Acids, 1990, Wiley). Each of these successes yields information about its respective target. Vigorous application of the technique can reveal the sequence of amino acids involved in binding, and effectively paint a picture of the active site in an enzyme.

Photolysis of a photoactivatable (photoreactive) moiety generates an intermediate which may react to result in a crosslink (covalent bond) to another molecule. Several classes of reactive intermediates have been exploited in photoaffinity labeling; the predominant ones being radicals, nitrenes, and carbenes. FIG. 4 herein depicts a first aspect of the invention, in which photoactivatable moieties capable of extruding (or eliminate) molecular nitrogen are photoactivated by long wavelength light to generate an active intermediate that forms a covalent bond with another molecule, such as a component of a cell. The invention, however, is not limited to cases involving the extrusion of molecular nitrogen. Instead, the discovery that long wavelength light is capable of photoactivating a moiety, such as, but not limited to, azo-type moieties, is generally applicable to any moiety that absorbs light at one or more long wavelengths. Past cross-linking with azo-type moieties was performed with light in the ultraviolet region of the spectrum, for example, at a short wavelength of 254 nm (see Fleming, S. A. 1995 Tetrahedron 51: 12479–12520).

In another aspect of the invention, methods are provided for introducing such photoactivatable moieties into active compounds such that upon photoactivation with long wavelength light, the compounds are cross-linked to a target molecule. Such modified compounds may be used in the treatment of living cells or tissue, where the use of long wavelength light is preferred because of its greater penetration characteristics. In preferred embodiments of the invention, the compound to be modified is a photosensitizing compound. More preferred is the derivatization of the periphery of a polypyrrolic macrocycle, such as a porphyrin macrocycle, to have an azo-type cross-linking moiety. Unexpectedly, the methods only require the presence of a vinyl group on the periphery of the macrocycle for introduction of a pyrazoline moiety.

The present invention thus also provides photosensitizer agents that may be crosslinked to target molecules and tissues (e.g. cellular molecules or macromolecules). By covalently attaching a photosensitizer agent to a desired target molecule, cell or tissue, irradiation could be carried out after the drug has cleared from normal, non-target tissue. Also, multiple applications of light to the target-bound photosensitizer would be possible, thereby eliminating a requirement for multiple administrations of photosensitizer. The invention also provides methods of photodynamic therapy comprising smaller doses of photosensitizer that can be selectively bound to a target molecule, cell or tissue. Such reduced doses would produce fewer unintended side effects on healthy tissue.

The invention thus provides a new class of active agents capable of being crosslinked by long wavelength light, although short wavelength light may also be used if desired. In one preferred embodiment, the active agents are polypyrrolic derivatives comprising a pyrazoline moiety. More preferred are polypyrrolic derivatives that are porphyrin based, chlorin based, bacteriochlorin based or isobacteriochlorin based. Such compounds are optionally substituted at the meso positions. The most preferred compounds of the invention have absorption/activation spectra that makes them suitable for use in therapeutic or industrial applications, including treatment of human beings and animals or application in agricultural or commercial processes.

Formulas representing compounds of the invention are shown in FIGS. 1–3. Exemplary compounds of the invention include salts of molecules having the formulas shown in the figures. The possible tautomeric forms of all disclosed compounds are of course also encompassed by the invention. Other outer ring positions of the disclosed macrocyclic compounds may also be substituted with one or more substituents as disclosed herein.

The invention also provides methods of preparing the compounds of the invention. For the preparation of pyrazoline containing compounds, the methods are surprisingly simple in reacting diazomethane with a polypyrrolic macrocycle that contains a vinyl moiety on the outer periphery. The resulting compounds may be used directly for photosensitizing applications, such as PDT, directly or under conditions wherein the compound is photocrosslinked to another molecule.

For the preparation of compounds represented by the formulas in FIG. 3, the disclosed methods may be considered as being composed of a series of reactions, each of which results in the preparation of a different derivative encompassed by the formulas. The methods may be viewed as beginning with a formylation reaction to form a formyl derivative followed by reaction to form a trifluoromethyl containing derivative. Further reaction produces a trifluoroacetyl containing derivative, which can be further reacted to form a trifluoromethyl oxime.

The invention also provides methods of using the compounds of the invention in photodynamic therapy for the treatment of various conditions, tissues and cells of a subject in need thereof. Such uses are based upon the ability of the disclosed compounds to generate singlet oxygen upon activation with irradiation containing at least one wavelength absorbed by a compound of the invention.

MODES OF CARRYING OUT THE INVENTION

Figure 4:
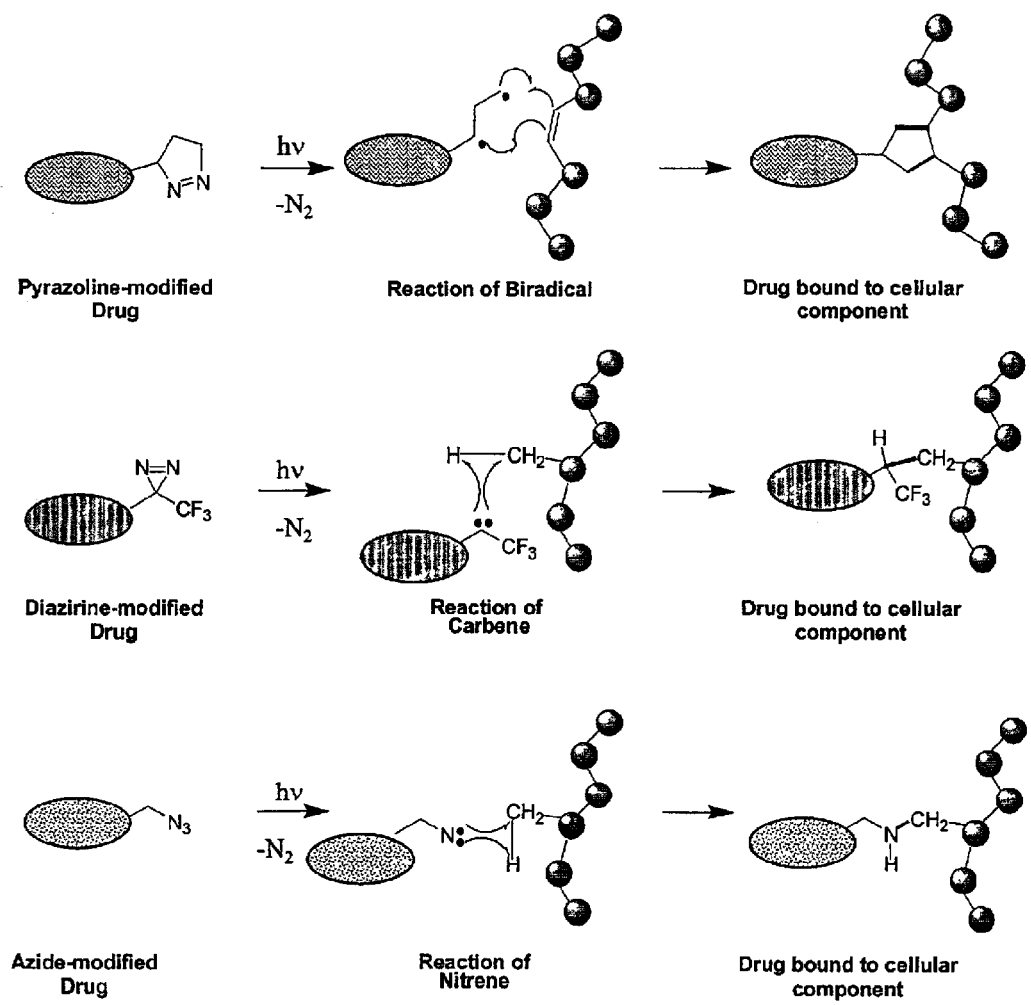
FIG. 4 is a schematic illustration of photoactivation to produce various functionalities with long wavelength light. The functionalities are a radical, a carbene, and a nitrene produced from the exemplary moieties of a pyrazoline, a diazirine, and an azide, respectively. All of the moieties are shown attached to an active agent (or "drug") to produce a "modified drug". Photoactivation of the moieties produces a reactive intermediate which reacts with a target (shown as a "cellular component") to crosslink the "drug" with the target. The "drug" may be an active agent, such as a photosensitizer, as discussed herein.

The present invention provides methods of photoactivating chemical moieties for crosslinking by the use of long wavelengths of light. This reflects the unexpected discovery that photoreactive compounds can be activated by long wavelength light between the short wavelengths of V, and near UV, light and thermal activation. In preferred embodiments of the invention, the chemical moieties give rise to reactive intermediates selected from nitrenes, carbenes and radicals. Azo-type (N=N) functionalities are known to form biradical (Engel, P. S.;Nalepa, C. J. Pure Appl. Chem. 1980, 52, 2621–2632), carbene (Tschirret-Guth, R. A., Medzihradsky, K. F., Ortiz de Montellano P. R. J. Am. Chem. Soc. 1999, 4731–4737), or nitrene (Durr; Kober Top. Curr. Chem. 1976, 66, 89–114) intermediates upon irradiation and are utilized in preferred embodiments of the invention. These highly reactive intermediates can crosslink carbon-carbon multiple bonds, or insert into carbon-hydrogen (C—H) bonds within targeted cells (see Fleet, G. W. J.; Porter, R. R.; Knowles, J. R. Nature 1969, 224, 511; Schrock, A. K.; Schuster, G. B. J. Am. Chem. Soc. 1984, 106, 5228–5234; and Pascual, A.; Casanova, J.; Samuels, H. H. J. Biol. Chem. 1982, 257, 9640–9647) and as depicted in FIG. 4.

Examples of nitrene generating moieties with which the invention may be practiced are known in the art and include the azides as a preferred class of photoreactive groups. Simple azides represented by —$(CH_2)_n$—$N_3$ wherein n is from 1 to 6. The azide class also includes arylazides ($C_6R_5N_3$) such as phenyl azide and particularly 4-fluoro-3-nitrophenyl azide, acyl azides (—$CON_3$) such as benzoyl azide and p-methylbenzoyl azide, azido formates (—$OCON_3$) such as ethyl azidoformate, phenyl azidoformate, sulfonyl azides (—$SO_2N_3$) such as benzenesulfonyl azide, and phosphoryl azides $(RO)_2PON_3$ such as diphenyl phosphoryl azide and diethyl phosphoryl azide. Another class of photoreactive groups for use in the present invention are diazo compounds, which include diazoalkanes (—$CHN_2$) such as diazomethane and diphenyldiazomethane, diazoketones (—$COCHN_2$) such as diazoacetophenone and 1-trifluoromethyl-1-diazo-2-pentanone, diazoacetates (—$OCOCHN_2$) such as t-butyl diazoacetate and phenyl diazoacetate, and beta-keto-alpha-diazoacetates (—CO—$CN_2$—CO—O—) such as t-butyl alpha diazoacetoacetate.

Examples of carbenes that may be used with the present invention include the diazirines (—$CHN_2$) such as 3-trifluoromethyl-3-phenyldiazirine, and ketenes (—CH=C=O) such as ketene and diphenylketene.

The invention may also be practiced with radicals, including biradicals, including pyrozaline and photoreactive aryl ketones such as, but not limited to, acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives.

In another aspect of the invention, the photoreactive moiety is attached to an active agent or drug such that photoactivation with long wavelength light covalently links (or crosslinks) the agent or drug to a target. The invention thus provides methods of derivatizing active agents to contain a photoreactive moiety. Preferred embodiments of the invention utilize a photosensitizer as the active agent.

The present invention thus provides methods of derivatizing a polypyrrolic macrocycle, such as, but not limited to, a porphyrin based photosensitizer (including chlorins, bacteriochlorins, or isobacteriochlorins) to contain a photoreactive moiety such as, but not limited to, a pyrazoline. A pyrazoline moiety can be readily introduced in place of a vinyl group on the periphery of a macrocycle (e.g. porphyrin, chlorin, bacteriochlorin, or isobacteriochlorin) molecule containing it by reaction with diazomethane. Preferably, the vinyl group is conjugated to the macrocycle's ring system. Alternatively, the vinyl group is attached to the porphyrin by means of a linker, preferably a linker of from one to 6 or 10 carbon atoms. The linker is preferably alkyl in nature. The polypyrrolic macrocycle may thus be photoactivated by long wavelength light to crosslink the macrocycle to its target(s). The pyrazoline moiety may also be converted to a cyclopropane moiety upon photoactivation to produce additional photosensitizer derivatives of the invention.

More than one photoreactive moieties may be introduced into an active agent (such as a photosensitizer). In the case of a pyrazoline, it depends on the number and position of vinyl groups on the macrocycle. In one embodiment of the invention, one or two pyrazoline moieties up to one pyrazoline per pyrrolic ring of the macrocycle. This is also applicable to other photoreactive groups. The invention also provides for the activation of one or more photoreactive moieties attached to an active agent with long (about 645 to about 700 nm) wavelength light, or when desired by the skilled practitioner, short (about 250 to about 300 or to about 425 nm) wavelength light.

The photoactivation of a photoreactive group, whether attached or not to an active agent, is preferably conducted by deliberate irradiation with long wavelength light rather than the result of spurious irradiation with ambient light from the environment or surroundings in general. Activation of a photoreactive group may be performed by incandescent or fluorescent light sources or photodiodes such as light emitting diodes directed to the location in which crosslinking is desired. Laser light can also be used for in situ delivery of light to a localized area. When applied to photocrosslinking in a patient, such as a clinical setting, the photoreactive group is first administered to the patient followed by irradiation, preferably after the group has localized to a target. Where the group is attached to an active agent, it may be localized based upon the nature of the active agent. In preferred embodiments of the invention, the light contains at least one wavelength in the range of about 645 to about 700 nm, more preferably from about 645 to about 650, from about 650 to about 655, from about 655 to about 660, from about 660 to about 665, from about 665 to about 670, from about 670 to about 675, from about 675 to about 680, from about 680 to about 685, from about 685 to about 690, from about 690 to about 695, and from about 695 to about 700 nm. Most preferred is light containing one or more wavelengths at 645, 650, 655, 660, 665, 670, 675, 680, 685, 690, 695, and 700 nm.

Figure 1:
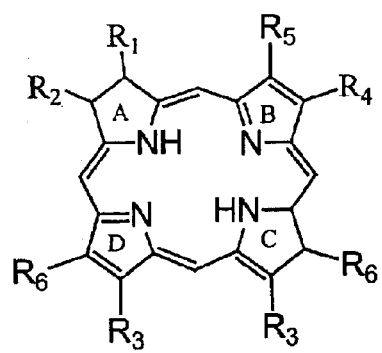
FIG. 1 depicts formulas representing porphyrin, chlorin, bacteriochlorin, and isobacteriochlorin derivatives of the invention.
Figure 1:
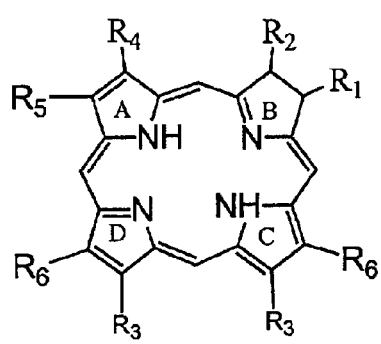
Figure 1:
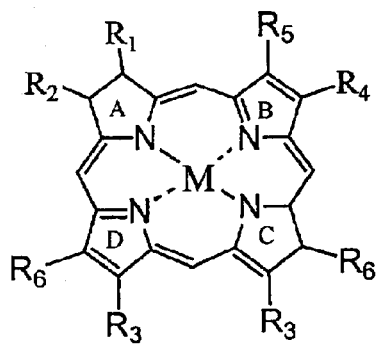
Figure 1:
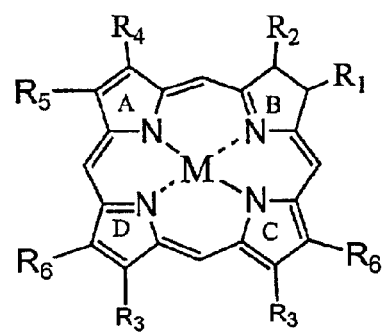

Pyrazoline containing photosensitizers of the invention are represented by the formulas in FIG. 1. The photosensitizer compounds of the invention include metallated forms of the photosensitizer wherein the metal is selected from Co, Ni(II), Cu(II), Zn(II), Fe(III), Sn, Ge, Si, Ga, Al, Mn(III), Gd(III), In and Tc. Positions $R_1$ and $R_4$ indicate the locations of a vinyl group which may be reacted with diazomethane to be the pyrazoline moiety (and through it the cyclopropane moiety).

Positions $R_2$, $R_5$ and $R_6$ are independently a hydrogen atom; a lower alkyl group, such as methyl, ethyl, n-propyl, isopropyl, t-butyl and n-pentyl; a lower alkyl carboxylic acid, such as formyl, carboxymethyl, carboxyethyl, carboxy-n-butyl, carboxy-sec-butyl, carboxy-n-hexyl or a salt, amide, ester or acylhydrazone thereof; a carboxylic acid ester (or carbalkoxy) group (2–6C), such as —COOCH$_3$, —CH$_2$CH$_2$COOCH$_3$, —CH$_2$CH$_2$COOCH$_2$CH$_3$, —CH$_2$CH(CH$_3$)COOCH$_2$CH$_3$, —CH$_2$CH$_2$CH$_2$COOCH$_2$CH$_2$CH$_3$, —CH$_2$CH(CH$_3$)COOCH$_2$CH$_3$; hydroxy; nitro; amino; sulfonyl; aryl (6–10C); aryl (6–10C) sulfonyl; aryl (6–10C) cyano; or —CONR$_7$CO— where R$_7$ is aryl (6–10C) or alkyl (1–6C).

Positions R$_2$, R$_5$ and R$_6$ may also be independently taken together with another ring, ring substituent or meso-substituent to form a fused 5- or 6-membered ring. The fused 5- or 6-membered ring so formed may be any saturated or unsaturated, carbocyclic or heterocyclic 5- or 6-membered ring that does not interfere with the osmylation and reduction reaction steps of the invention. Examples of such rings include cyclopentane, furan, thiophene, pyrrole, isopyrrole, 3-isopyrrole pyrazole, 2-isoimidazole, 1,2,3-triazole, 1,2,4-triazole, 1,2-dithiole, 1,3-dithiole, 1,2,3-oxathiole, isoxazole, oxazole, thiazole, isothiazole, 1,2,3-oxadiathiazole, 1,2,4-oxadiazole, 1,2,5-oxadiazole, 1,3,4-oxadiazole, 1,2,3-dioxazole, 1,2,4-dioxazole, 1,2,5-oxathiazole, 1,3-oxathiole, benzene, cyclohexane, 1,2-pyran, 1,4-pyran, 1,2-pyrone, 1,4-pyrone, 1,2-dioxin, 1,3-dioxin (dihydro form), pyridine, pyridazine, pyrimidine, pyrazine, piperazine, 1,3,5-triazine, 1,2,4-triazine, 1,2,4-oxazine, 1,3,2-oxazine, o-isoxazine, 1,2,5-oxathiazine, 1,4-oxazine, p-isoxazine, 1,2,6-oxathiazine, 1,3,5,2-oxadiazine, morpholine, azepine, oxepin, thiepin, 1,2,4-diazepine, and the like. Preferably, when the positions are used as part of a fused, 5- to 6-membered ring, the ring is a 6-membered ring. Most preferably, when the positions are used as part of a ring, it is a 6-membered carbocyclic ring, i.e., a benzene ring.

Each R$_3$ is independently hydrogen; hydroxy; a lower alkyl carboxylic acid, such as formyl, carboxymethyl, carboxyethyl, carboxy-n-butyl, carboxy-sec-butyl, carboxy-n-hexyl or a salt, amide, ester or acylhydrazone thereof; nitro; amino; a carboxylic acid ester (or carbalkoxy) group (2–6C), such as —COOCH$_3$, —CH$_2$CH$_2$COOCH$_3$, —CH$_2$CH$_2$COOCH$_2$CH$_3$, —CH$_2$CH(CH$_3$)COOCH$_2$CH$_3$, —CH$_2$CH$_2$CH$_2$COOCH$_2$CH$_2$CH$_3$, —CH$_2$CH(CH$_3$)COOCH$_2$CH$_3$; sulfonyl; aryl (6–10C); aryl (6–10C) sulfonyl; aryl (6–10C) cyano; or —CONR$_7$CO— where R$_7$ is aryl (6–10C) or alkyl (1–6C).

The meso positions between the pyrrolic rings of the formulas may optionally be independently substituted. Exemplary substitutions include a large number of substituted or unsubstituted alkyl groups, substituted or unsubstituted cycloalkyl groups (preferably containing from about 3 to about 7 carbon atoms, such as, but not limited to, cyclopropyl, cyclohexyl, and cycloheteroalkyl, such as glucopyranose or fructofuranose sugars), and aryl or aromatic rings. When one or more of the positions is an alkyl group, they preferably have from about 1 to about 18 carbon atoms, more preferably about 1 to 12 carbon atoms and, even more preferably, about 1–6 carbon atoms. Examples of typical alkyl groups include methyl, ethyl, isopropyl, sec-butyl, tert-butyl, n-pentyl and n-octyl. Examples of substitutions on an alkyl group include a halogen atom, such as fluorine, chlorine or bromine; a hydroxy group, such as in pentoses and hexoses; thiol; or a carbonyl group, such as when the alkyl group is an aldehyde, ketone, carboxylic acid (e.g., a fatty acid) or ester or amide; a primary, secondary, tertiary, or quaternary amino group; nitrile; a phosphate group; a sulfonate group; and the like.

When one or more of the positions is an aryl group, it preferably contains from about 5 to about 12 carbon atoms, optionally containing one or more heteroatoms, and optionally including rings that are fused to the existing conjugated porphyrin ring structure. Examples of suitable aromatic rings include furan, thiophene, pyrrole, isopyrrole, 3-isopyrrole, pyrazole, 2-isoimidazole, 1,2,3-triazole, 1,2,4-triazole, 1,2-dithiole, 1,3-dithiole, 1,2,3-oxathiole, isoxazole, oxazole, thiazole, isothiazole, 1,2,3-oxadiazole, 1,2,4-oxadiazole, 1,2,5-oxadiazole, 1,3,4-oxadiazole, 1,2,3-4-oxatriazole, 1,2,3,5-oxatriazole, 1,2,3-dioxazole, 1,2,4-dioxazole, 1,3,2-dioxazole, 1,3,4-dioxazole, 1,2,5-oxathiazole, 1,3-oxathiole, benzene, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazone, 1,2,4-triazine, 1,2,3-triazine, 1,2,4-oxazine, 1,3,2-oxazine, 1,3,6-oxazine, 1,4-oxazine, o-isoxazine, p-isoxazine, 1,2,5-oxathiazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, naphthalene, 1,2-benzopyran, 1,2-benzopyrone, 1,4-benzopyrone, 2,1-benzopyrone, 2,3-benzopyrone, quinoline, isoquinoline, 1,2-benzodiazine, 1,3-benzodianzine, naphthyridine, pyrido[3,4-b]-pyridine, pyrido[3,2-b]-pyridine, pyrido[4,3-b]-pyridine, 1,3,2-benzoxazine, 1,4,2-benzoxazine, 2,3,1-benzoxazine, 3,1,4-benzoxazine, 1,2-benzisoxazine, 1,4-benzisoxazine, anthracene, phenanthrene, carbazole, xanthene, acridine, purine, steroidal compounds and the like.

In a particularly preferred embodiments, the positions are independently phenyl, phenol, alkyl(1–6C), naphthyl, pyridinyl, lower N-alkyl pyridinium salts, and aryl (6–10C).

Alternatively, at least one of the positions is represented by the following formulas

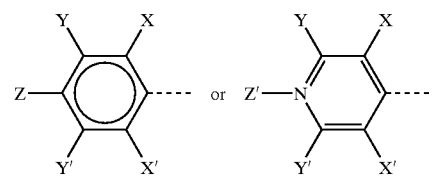

wherein X, Y, Z, X', Y' and Z' are independently (1) hydrogen; (2) halogen, such as fluoro, chloro, iodo and bromo; (3) lower alkyl, such as methyl, ethyl, n-propyl, isopropyl, t-butyl, n-pentyl and the like groups; (4) lower alkoxy, such as methoxy, ethoxy, isopropoxy, n-butoxy, t-pentoxy and the like; (5) hydroxy; (6) carboxylic acid or acid salt, such as —CH$_2$COOH, —CH$_2$COO—Na$^+$, —CH$_2$CH(Br)COOH, —CH$_2$CH(CH$_3$)COOH, —CH (Cl)—$CH_2$—$CH(CH_3)$—COOH, —$CH_2$—$CH_2$—$C(CH_3)_2$—COOH, —$CH_2$—$CH_2$—$C(CH_3)_2$—$COO^-K^+$, —$CH_2$—$CH_2$—$CH_2$—$CH_2$—COOH, $C(CH_3)_3$—COOH, $CH(Cl)_2$—COOH and the like; (7) carboxylic acid ester, such as —$CH_2CH_2COOCH_3$, —$CH_2CH_2COOCH_2CH_3$, —$CH_2CH(CH_3)COOCH_2CH_3$, —$CH_2CH_2CH_2COOCH_2CH_2CH_3$, —$CH_2CH(CH_3)_2COOCH_2CH_3$, and the like; (8) sulfonic acid or acid salt, for example, group I and group II salts, ammonium salts, and organic cation salts such as alkyl and quaternary ammonium salts; (9) sulfonic acid ester, such as methyl sulfonate, ethyl sulfonate, cyclohexyl sulfonate and the like; (10) amino, such as unsubstituted primary amino, methylamino, ethylamino, n-propylamino, isopropylamino, 5-butylamino, sec-butylamino, dimethylamino, trimethylamino, diethylamino, triethylamino, di-n-propylamino, methylethylamino, dimethyl-sec-butylamino, 2-aminoethanoxy, ethylenediamino, 2-(N-methylamino)heptyl, cyclohexylamino, benzylamino, phenylethylamino, anilino, N-methylanilino, N,N-dimethylanilino, N-methyl-N-ethylanilino, 3,5-dibromo-4-anilino, p-toluidino, diphenylamino, 4,4'-dinitrodiphenylamino and the like; (11) cyano; (12) nitro; or (13) a biologically active group.

The term "biologically active group" can be any group that selectively promotes the accumulation, elimination, binding rate, or tightness of binding in a particular biological environment. For example, one category of biologically active groups is the substituents derived from sugars, specifically, (1) aldoses such as glyceraldehyde, erythrose, threose, ribose, arabinose, xylose, lyxose, allose, altrose, glucose, mannose, gulose, idose, galactose, and talose; (2) ketoses such as hydroxyacetone, erythrulose, rebulose, xylulose, psicose, fructose, sorbose, and tagatose; (3) pyranoses such as glucopyranose; (4) furanoses such as fructofuranose; (5) O-acyl derivatives such as penta-O-acetyl-I-glucose; (6) O-methyl derivatives such as methyl I-glucoside, methyl β-glucoside, methyl I-glucopyranoside, and methyl-2,3,4,6-tetra-O-methyl-glucopyranoside; (7) phenylosazones such as glucose phenylosazone; (8) sugar alcohols such as sorbitol, mannitol, glycerol, and myo-inositol; (9) sugar acids such as gluconic acid, glucaric acid and glucuronic acid, L-gluconolactone, L-glucuronolactone, ascorbic acid, and dehydroascorbic acid; (10) phosphoric acid esters such as I-glucose 1-phosphoric acid, I-glucose 6-phosphoric acid, I-fructose 1,6-diphosphoric acid, and I-fructose 6-phosphoric acid; (11) deoxy sugars such as 2-deoxy-ribose, rhamnose (deoxy-mannose), and fucose (6-deoxy-galactose); (12) amino sugars such as glucosamine and galactosamine; muramic acid and neuraminic acid; (13) disaccharides such as maltose, sucrose and trehalose; (14) trisaccharides such as raffinose (fructose, glucose, galactose) and melezitose (glucose, fructose, glucose); (15) polysaccharides (glycans) such as glucans and mannans; and (16) storage polysaccharides such as I-amylose, amylopectin, dextrins, and dextrans.

Amino acid derivatives are also useful biologically active substituents, such as those derived from valine, leucine, isoleucine, threonine, methionine, phenylalanine, tryptophan, alanine, arginine, aspartic acid, cystine, cysteine, glutamic acid, glycine, histidine, proline, serine, tyrosine, asparagine and glutamine. Also useful are peptides and polypeptides (up to 50 or 100 amino acids or more), particularly those known to have affinity for specific receptors, for example, oxytocin, vasopressin, bradykinin, LHRH, thrombin and the like. Antibodies, or antigen binding fragments thereof, may also be used.

Another useful group of biologically active substituents are those derived from nucleosides, for example, ribonucleosides such as adenosine, guanosine, cytidine, and uridine; and 2'-deoxyribonucleosides, such as 2'-deoxyadenosine, 2'-deoxyguanosine, 2'-deoxycytidine, and 2'-deoxythymidine.

Another category of biologically active groups that is particularly useful is any ligand that is specific for a particular biological receptor. The term "ligand specific for a receptor" refers to a moiety that binds a receptor at cell surfaces, and thus contains contours and charge patterns that are complementary to those of the biological receptor. The ligand is not the receptor itself, but a substance complementary to it. It is well understood that a wide variety of cell types have specific receptors designed to bind hormones, growth factors, or neurotransmitters. However, while these embodiments of ligands specific for receptors are known and understood, the phrase "ligand specific for a receptor", as used herein, refers to any substance, natural or synthetic, that binds specifically to a receptor.

Examples of such ligands include: (1) the steroid hormones, such as progesterone, estrogens, androgens, and the adrenal cortical hormones; (2) growth factors, such as epidermal growth factor, nerve growth factor, fibroblast growth factor, and the like; (3) other protein hormones, such as human growth hormone, parathyroid hormone, and the like; and (4) neurotransmitters, such as acetylcholine, serotonin, dopamine, and the like. Any analog of these substances that also succeeds in binding to a biological receptor is also included.

Figure 2:
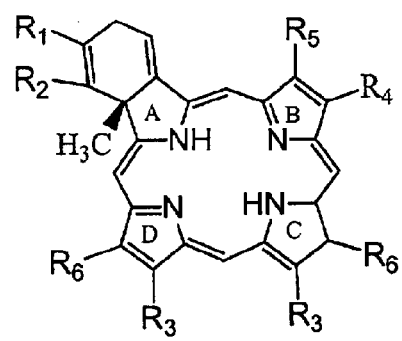
FIG. 2 depicts formulas representing additional porphyrin based derivatives of the invention.
Figure 2:
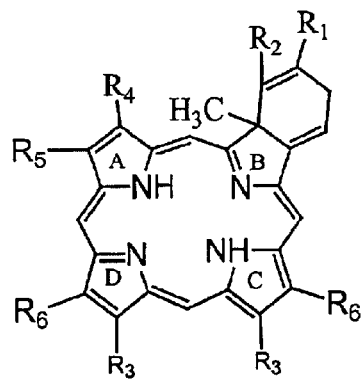
Figure 2:
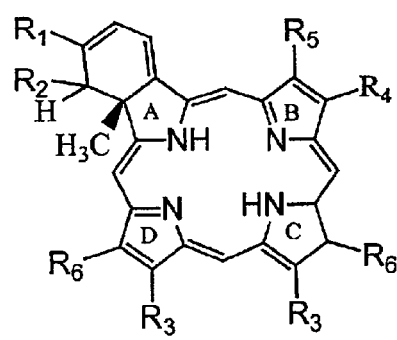
Figure 2:
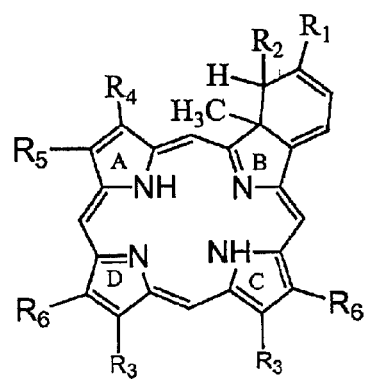
Figure 2:
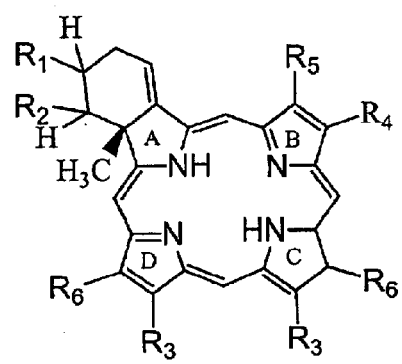
Figure 2:
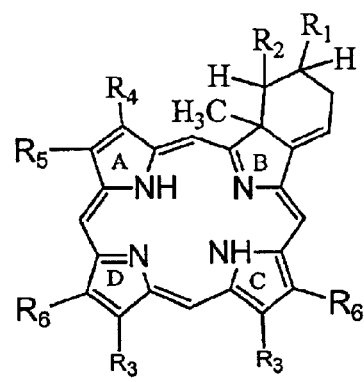

Additional pyrazoline (and cyclopropane) containing photosensitizers of the invention are represented by the formulas in FIG. 2. As noted above, the photosensitizer compounds may be metallated forms wherein the metal is selected from Co, Ni(II), Cu(II), Zn(II), Fe(III), Sn, Ge, Si, Ga, Al, Mn(III), Gd(III), In and Tc. Position $R_4$ represents a vinyl group which may be reacted with diazomethane to be the pyrazoline moiety (and through it the cyclopropane moiety). Positions $R_1$, $R_2$, $R_3$, $R_5$ and $R_6$, as well as the meso positions between the pyrrolic rings of the macrocycle, are substituted as discussed above.

Figure 3:
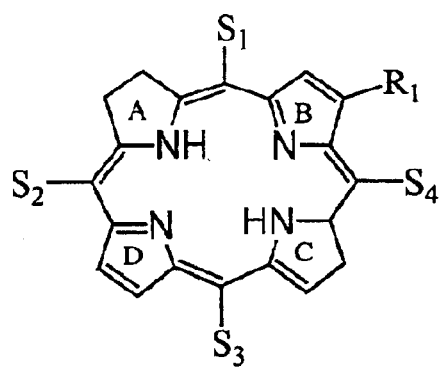
FIG. 3 depicts formulas representing additional photosensitizer derivatives of the invention.
Figure 3:
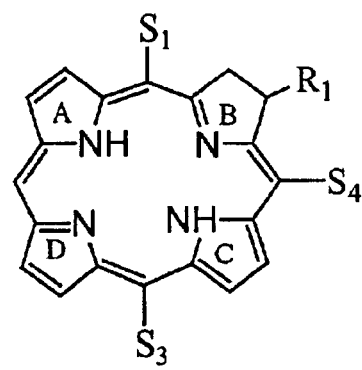
Figure 3:
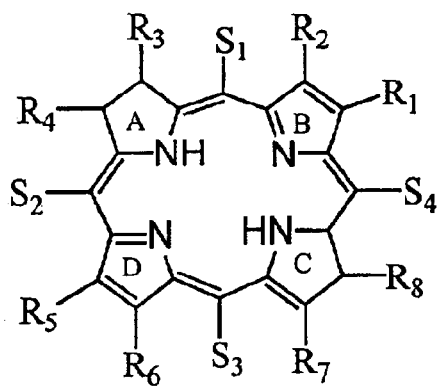
Figure 3:
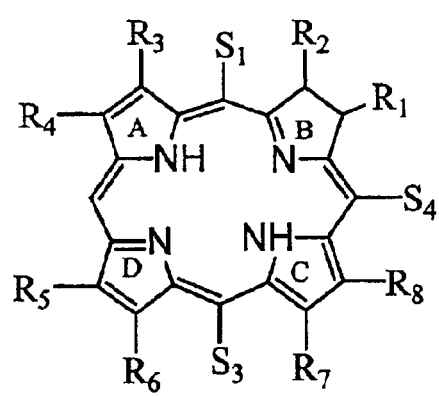

The formulas in FIG. 3 represent additional photosensitizer derivatives of the invention, wherein two or more of the meso positions between the pyrrolic rings are substituents as defined for the meso positions discussed above. As such, the formulas represent derivatives or analogs of tetraphenylporphyrin and diphenylporphyrin. Particularly preferred derivatives include those based on Foscan®, wherein all four meso positions are phenol groups with the —OH para to the meso position.

In formula 3A, R$_1$ is formyl or has the structure

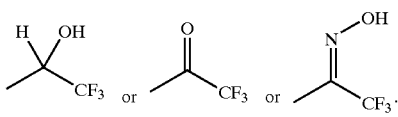

In formula 3B, either R$_1$ or the meso position S$_4$ is formyl or has one of the above three structures.

In both formulas, the periphery of the macrocycle, composed of the positions of rings A, C, and D corresponding to positions R$_2$ through R8 are independently a hydrogen atom; a lower alkyl group, such as methyl, ethyl, n-propyl, isopropyl, t-butyl and n-pentyl; a lower alkyl carboxylic acid, such as formyl, carboxymethyl, carboxyethyl, carboxy-n-butyl, carboxy-sec-butyl, carboxy-n-hexyl or a salt, amide, ester or acylhydrazone thereof; a carboxylic acid ester (or carbalkoxy) group (2–6C), such as —COOCH$_3$, —CH$_2$CH$_2$COOCH$_3$, —CH$_2$CH$_2$COOCH$_2$CH$_3$, —CH$_2$CH(CH$_3$)COOCH$_2$CH$_3$, —CH$_2$CH$_2$CH$_2$COOCH$_2$CH$_2$CH$_3$, —CH$_2$CH(CH$_3$)COOCH$_2$CH$_3$; hydroxy; nitro; amino; sulfonyl; aryl (6–10C); aryl (6–10C) sulfonyl; aryl (6–10C) cyano; or —CONR$_7$CO— where R$_7$ is aryl (6–10C) or alkyl (1–6C). Alternatively, one or more of the positions is taken together with another ring, ring substituent or meso-substituent to form a fused 5- or 6-membered ring as described above with respect to the formulas of FIG. 1.

The present invention also provides methods of conducting photodynamic therapy (PDT) by use of any of the disclosed photosensitizers. Such methods generally include contacting a target with a photosensitizer and irradiating said photosensitizer with light containing at least one wavelength which activates said photosensitizer. In one embodiment of the invention, the target may be living cells or tissues or a bodily fluid (such as blood). PDT may of course be conducted in vitro, ex vivo, or in vivo. When conducted in vivo, the photosensitizer is administered to a subject, such as a human patient, in need of PDT. If systemically administered, the photosensitizer is allowed to localize in the target cells or tissue before irradiation. In PDT methods comprising photocrosslinking photosensitizers of the invention, the light used for PDT photoactivation preferably also contains a wavelength of light which photocrosslinks the photosensitizer to the target. Most preferred is the use of light containing a single wavelength of light which photoactivates both PDT and photocrosslinking. After photocrosslinking, PDT may be repeated simply by repeating irradiation; there would be no requirement for further administration of the photosensitizer before irradiation.

The invention also provides a form of "passive" PDT after photocrosslinking of a photosensitizer to a target molecule, cell, or tissue. This "passive" PDT occurs through photoactivation of the crosslinked photosensitizer via ambient light (such as light from indoor light sources or the sun) containing at least one wavelength of light which photoactivates the photosensitizer for PDT. Such ambient light is distinct from deliberate irradiation of a target tissue with light, such as a laser or light emitting diode. This provides a means for continued PDT even in the absence of deliberate irradiation. This aspect of the invention is preferably practiced with reduced dosages of the photosensitizer because clearance thereof from the target is reduced after photocrosslinking has occurred. This provides a new means of continued PDT, analogous to time release of an active chemical agent or the implantation of radioactive materials, for conditions such as cancer and chronic diseases.

A serendipitous discovery resulted in the discovery of pyrazoline derivatives of photosensitizers as provided by the present invention. An esterification reaction involving diazomethane and benzoporphyrin diacid (see below) resulted in a myriad of products in addition to the expected esters of the proprionic acids.

BPD-diacid

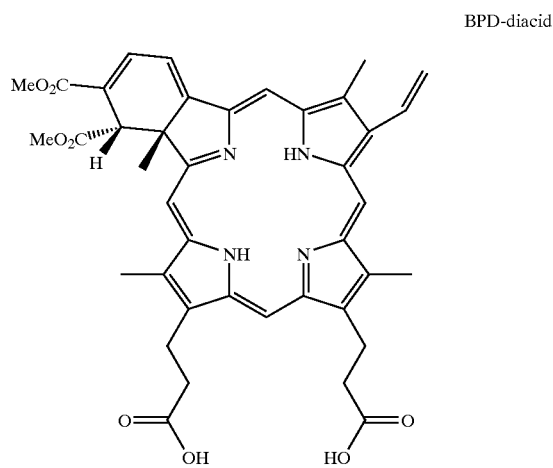

The products are expected to be products of diazomethane reacting with the activated olefins of the benzoporphyrin, and similar reactions of diazomethane and protoporphyrin, 7 (the dehydrated version of the naturally occurring starting material for many photosensitizers), was used to generate three addition products. The three pyrazoline porphyrins (8–10) are shown in Scheme 1 below.

Scheme 1
Reaction of Protoporphyrin and Diazomethane

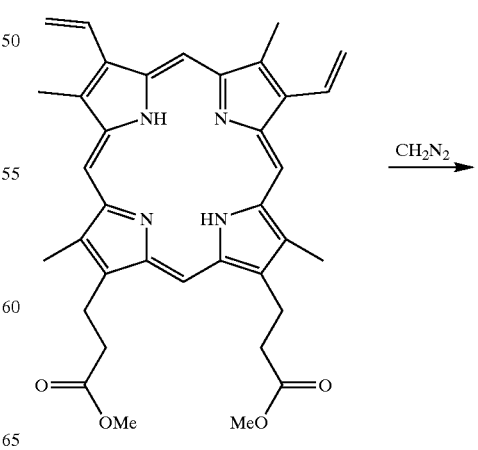

7

-continued

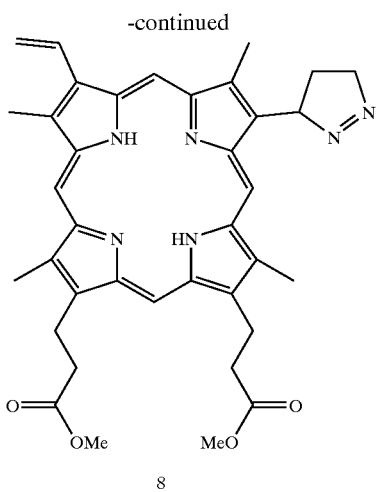

8

+

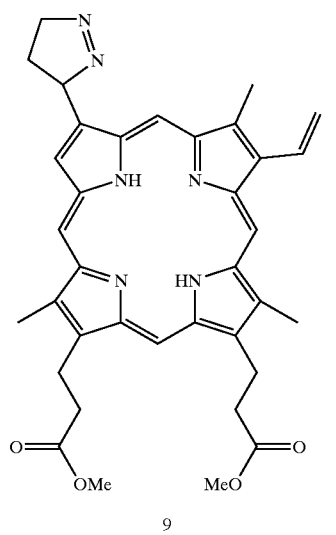

9

+

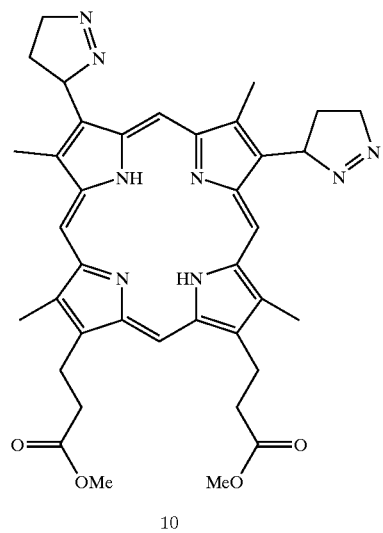

10

Optimization and full characterization of the aforementioned reaction and products was conducted. The yields obtained are respectable (77% recovery for reaction Scheme 1), but in order to isolate sufficient amounts of the single adduct pyrazolines (8 and 9), the reaction must be stopped before completion. Thus the overall conversion of starting material to products must be high, but if a huge excess of diazomethane is present and left to react, the single adducts will proceed to form the diadduct.

The reaction was complicated by the formation of gaseous diazomethane, carried by an ethereal distillate, upon base catalyzed decomposition of N-methyl-N-nitroso amines (Black, T. H. Aldrichimica Acta 1983, 16, 3–10). Additionally, and under dilute porphyrin solution conditions, the conversion to products was very poor. Methylene chloride was found to be the best solvent for protoporphyin dimethylester. The most successful reactions included dissolving the nitroso compound in a minimum amount of ether and adding more methylene chloride to the stirring reaction mixture upon complete addition of diazomethane.

Most references for diazomethane reactions (see Pizey, J. S. In "Synthetic Reagents"; Halsted: New York, 1974; Vol. II, Chapter 4) on small molecules cite usage of an excess of approximately 10:1, diazomethane:substrate. With high molecular weight porphyrins and their inherent low solubility it was found that a molar ratio of 50:1, diazomethane:porphyrin is preferred. In addition, because the reaction must be left for 12 hours, a method of containing the gaseous diazomethane in the reaction mixture was required. On several occasions, built-up pressure resulted in septa that were either blown off the reaction flask, or torn open. An approach was found in sealing a balloon (a "diazo balloon") over the reaction flask to contain the reactants but allow for expansion.

Characterization of the above three products is discussed in Example 10 below. The compounds are believed to be the first example of pyrazoline-modified protoporphyrins. There is precedence for the regioselectivity of diazomethane reactions with many familiar substrates, but none could be found involving a conjugated vinyl group of a porphyrin. As such, the ability to produce pyrazoline modified porphyrins via a conjugated vinyl group was surprising as discussed below.

Without being bound by theory, the pyrazoline adducts are believed to be formed as a result of a concerted $[4\pi+2\pi]$ cycloaddition (Carey, F. A.; Sundgberg, R. J. In "Advanced Organic Chemistry"; Plenum Press: New York, 1990, Third Ed., p.635). The 1,3 dipolar molecule is diazomethane, and the vinyl group is the dipolarophile. Most examples in the literature cite diazomethane reactions with electron-poor species (Black, T. H. supra), or with alkenes conjugated to strong electron-withdrawing substituents. It was thus quite surprising to find that vinyl groups conjugated to the incredibly electron-rich porphyrin system, reacted to form the products.

The present invention also provides pyrazoline adducts of chlorin and bacteriochlorin based photosensitizers. Methylpyropheophorbide (MePPP, 18) and its derivatives are suitable for use as PDT agents. MePPP is a chlorin and an effective producer of singlet oxygen.

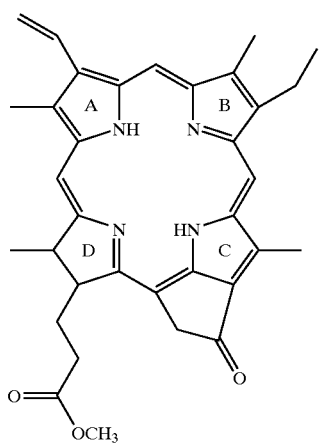

This chromophore has an appreciable absorption in the visible region at wavelengths greater than 630 nm. Derived from a natural product (isolatable from spinach), MePPP consists of a single isomer, with several derivatives demonstrated to have an ability to localize in desired tissue, and cleared from the body in a relatively short time post-irradiation (Mettath, S.; Shibata, M.; Alderfer, J. L; Senge, M. O.; Smith, K. M.; Rein, R.; Dougherty, T. J.; Pandey, R. K. *J. Org. Chem.* 1998, 63, 1646–1656). Surprisingly, multiple products did not result from the reaction of diazomethane and 18. The reaction of diazomethane with ketones is known and has been studied for some time. In the case of cyclic ketones, such as the one in the exocyclic ring fused with the C-ring of 18, the dominant reaction pathway is expected to be ring expansion. This can be complicated by the conflicting migratory aptitude of the involved carbon atoms (Newton, R. F.; Wadsworth, A. H. *J. Chem. Soc., Perkin Trans. I* 1982, 823), and reaction of the product with excess diazomethane to produce undesired higher homologues (Wiberg, K. B.; O'Donnell, M. J. *J. Am. Chem. Soc.* 1979, 101, 6660).

The reaction of diazomethane and 18 to form a single main product was thus unexpected, although on one occasion when the reaction was left for an extended period of time, a second product was visible by TLC ($R_f$=0.2 vs. $R_{f19}$=0.44 and $R_{f18}$=0.67, 10% EtAce/$Ch_2Cl_2$ eluent). The main product of the reaction is the pyrazoline of MePPP (19), shown below with it numbering of the carbon atoms.

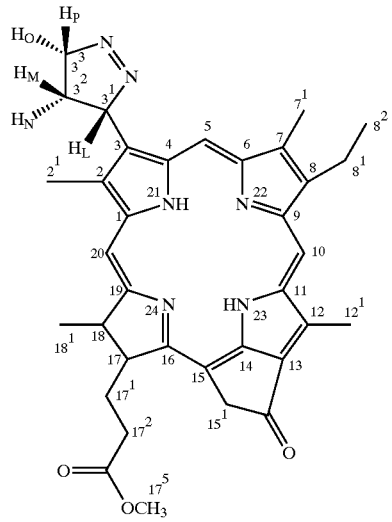

The increased solubility of MePPP in $CH_2Cl_2$ (compared with PP-DME) facilitated its reaction with diazomethane. A large excess of diazomethane: porphyrin (50:1) was still required, but the ability to allow the reaction could go to completion to form only one product simplified isolation. The product was purified by column chromatography to give a final yield of 78% yield. The structure was assigned based upon the UV-vis spectrum, NMR spectrum, and HMQC correlations as well as comparisons to pyrazoline adducts of PP-DME. The reaction of diazomethane with the vinyl group of a chlorin provides an unambiguous means of introducing the pyrazoline moiety to this photosensitizer.

Thermal Stability

It is well known that cyclic azo compounds including heteroaromatics with a N=N bond of strong double-bond character, such as pyrazolines, can eliminate molecular nitrogen on addition of sufficient thermal energy or on electronic excitation (Meier, H.; Zeller, K. P. *Angew. Chem. Int. Ed. Engl.* 1977, 16, 835). Application of porphyrin pyrazolines as crosslinking agents in PDT occurs at physiological temperatures.

It was anticipated that protoporphyrin pyrazolines would also undergo a thermal cycloelimination reaction through the extrusion of nitrogen. Each of thy product pyrazolines was investigated for thermal stability towards cycloelimination by looking for decomposition products at a variety of temperatures in various refluxing solvents. The pyrazolines were found to sustain relatively high temperatures for extended periods of time with little or no decomposition. Even in refluxing toluene, they undergo conversion to their thermal products relatively slowly (Table 1).

TABLE 1

Thermolysis of pyrazoline adducts of PP-DME

| Pyrazoline | Time required for complete thermolysis (reflux in toluene) to cyclopropanes |
|---|---|
| B-ring Isomer (9) | 23 h |
| A-ring Isomer (8) | 21 h |
| Di-Adduct (10) | 47 h |

Both the A and B-ring pyrazoline adducts reacted cleanly to give a single product cyclopropane each. The thermal products were visible by TLC as faster moving pink spots ($R_{f15}$=0.55, and $R_{f16}$=0.53, 10% EtAce in $CH_2Cl_2$ eluent) above their respective pyrazolines ($R_{f8}$=0.18 and $R_{f9}$=0.21).

Figure 7:
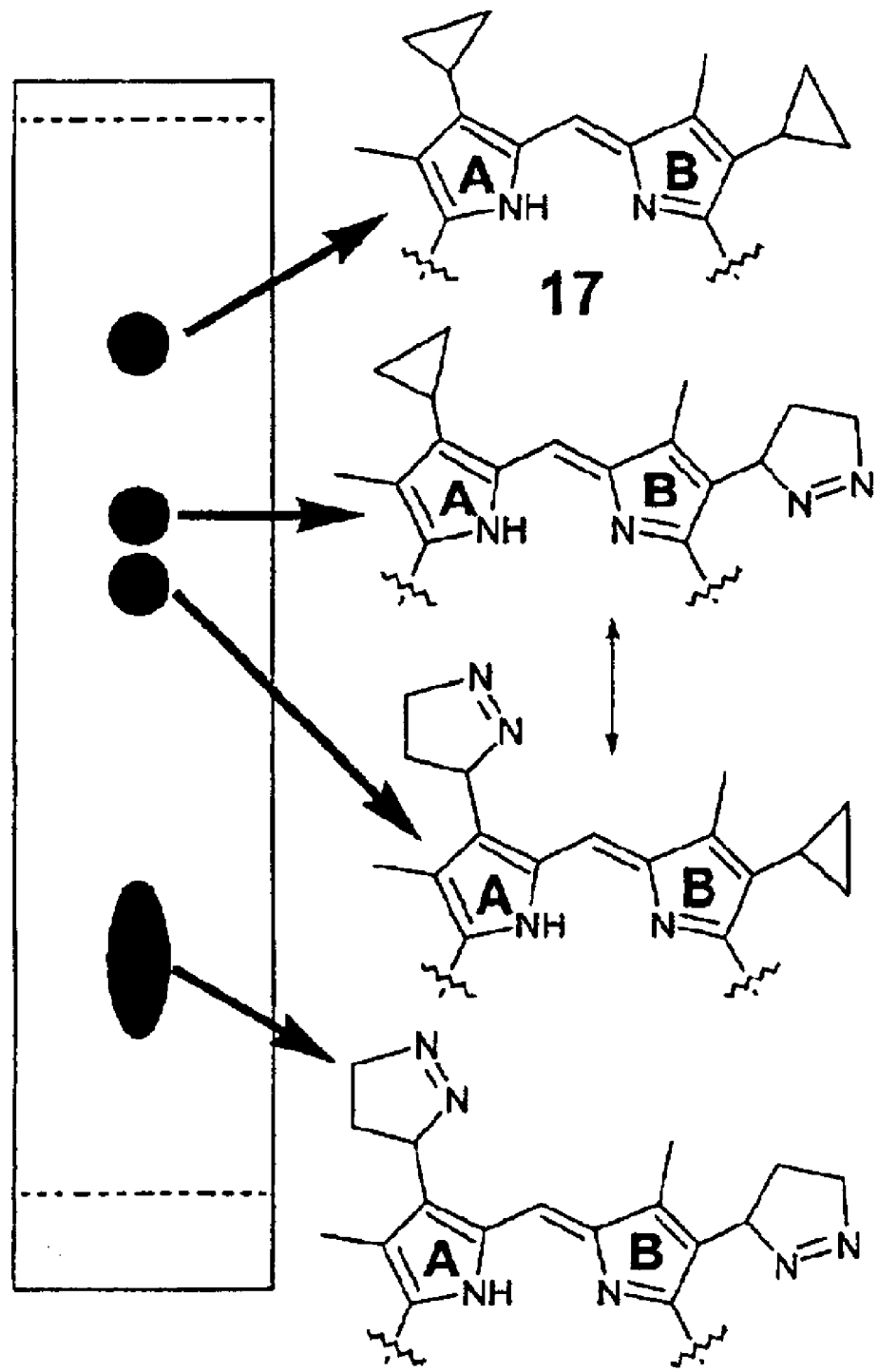
FIG. 7 shows a schematic of thin layer chromatography (TLC) plate analysis of the thermolysis of di-adduct pyrazoline (8% EtAce/CH$_2$Cl$_2$ eluent).

The di-adduct (10) formed three products in the course of the reaction. These are expected to be the two possible products formed by cycloelimination from the pyrazoline moieties on the A and B ring, and a third product from cycloelimination from both (17). This is illustrated in FIG. 7, where the two bands directly above the di-adduct pyrazoline represented the products whereby one ring-pyrazoline had reacted while the other remained intact, and the fastest moving band represented the porphyrin where both pyrazolines reacted to give the di-cyclopropane product (17). The two middle spots in the TLC were observed to disappear as the reaction proceeded.

The identities of the thermal products (15, 16, 17) were confirmed by MS, and by comparing the $R_f$ values and UV-vis spectra of the products in question to their photochemical counterparts, which were characterized extensively and discussed below.

Photochemical Activation

The protoporphyrin pyrazolines were for susceptibility to eliminate nitrogen on electronic excitation and create a reactive intermediate that will crosslink cellular components. The spectral characteristics (Rau, H. Angew. Chem. Inct. Ed. Engl. 1973, 12, 224) of the cis-azoalkanes (pyrazolines) indicate that the photochemical excitation process is n-π* derived. The n-π* absorption of a pyrazoline lies in the 300–400 nm range. Although the n-π* transition is much weaker (ca. 100-fold) than the π–π* transition ($\epsilon=10^4-10^5$), the lower energy light of the former is convenient for the photoextrusion of nitrogen from azoalkanes (Adam, W.; De Lucchi, O. Angew. Chem. Int. Ed. Engl. 1980, 19, 762–779).

Irradiation of degassed, dilute solutions [$3\times10^{-4}$M] of the compound 8, 9 and 10 in benzene with 350 nm light produced a single photoproduct in each case. Without being bound by theory, the photochemistry is thought to proceed initially through a diazenyl biradical intermediate (Hiberty, P. C.; Jean, V. J. Am. Chem. Soc. 1979, 101, 2538) (11a), followed by extrusion of nitrogen, yielding a biradical (11b), which reacts intramolecularly to form the cyclopropane (16). Scheme 2 illustrates the proposed reaction scheme for the A-ring pyrazoline (11).

Scheme 2
Photochemistry of the pyrazoline functionality

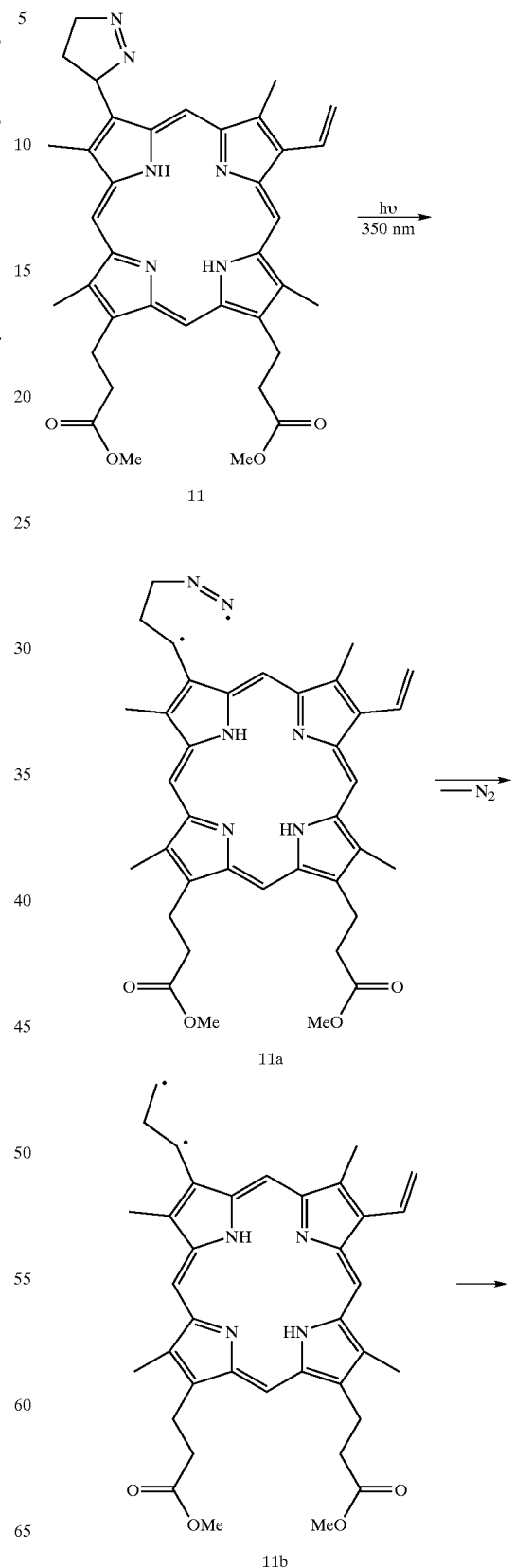

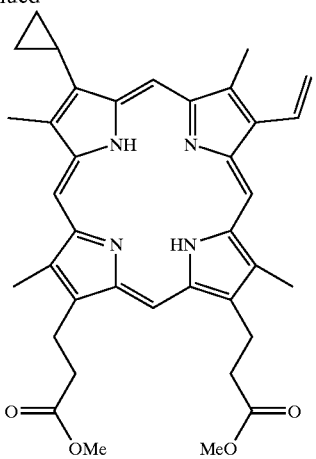

16

Analogous reactions would lead to the formation of the respective cyclopropanes (15 and 17) of the other mono-adduct (10) and the di-pyrazoline (12) as well. The photoproducts were visible by TLC, and appeared as a faster moving pink bands above the pyrazoline (identical $R_f$ values as the thermal products discussed above). Additional characterizations of the product cyclopropanes (15, 16, 17) were carried out by mass spectrometry, elemental analysis and $^1$H NMR spectroscopy, and are discussed in the Examples below.

A notable spectroscopic distinction between the di-adduct pyrazoline (12) and its photoproduct di-cyclopropane (17) is the absence of diastereomers in the latter. Formation of the cyclopropanes removes the stereocenters in the pyrazolines and the result is a single product visible in the NMR spectrum.

Figure 8:
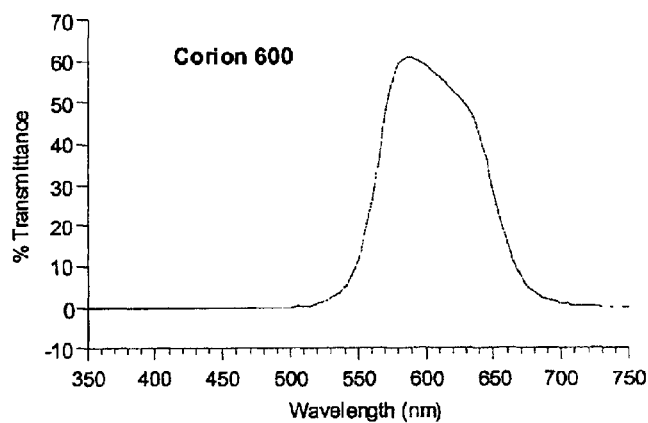
FIG. 8 shows the transmittance of a Corion 600 red light filter.

The use of long wavelength light to penetrate tissue during PDT was discussed above. Surprisingly, and in addition to the photochemical activation discussed above, long wavelength light was found to also be capable of activating the protoporphyrin pyrazolines. This unexpected finding supports the use of these compounds as PDT photosensitizers where red light activation may be beneficially utilized. Each of the A and B-ring pyrazolines (8 and 9), as well as the di-adduct pyrazoline (10) formed their respective cyclopropanes (15, 16, 17) on irradiation with filtered long-wavelength red light from a filtered source having the transmission spectrum shown in FIG. 8. Degassed dilute benzene solutions of the pyrazolines with similar concentrations to those irradiated with 350 nm light were exposed to the red light, and complete conversion to corresponding cyclopropanes (identical to those obtained with 350 nm irradiation) was achieved in approximately 48 hours.

The ability of low energy light to bring about the extrusion of molecular nitrogen was surprising since the pyrazoline chromophore is known to absorb between 300–350 nm. Thus, the efficient nitrogen extrusion to form the cyclopropanes using long wavelength irradiation is not expected.

The pyrazoline of methylpyropheophorbide (19) makes for an interesting photochemical study. A chlorin, this molecule has a strong Q-band absorption at 665 nm ($\epsilon$=52, 700, in benzene) whose intensity is almost half that of its Soret band (411 nm, $\epsilon$=107, 100). This region of the visible spectrum is particularly useful for light penetration through tissue. The following discussion of photochemistry of a pyrazoline modified chlorin from irradiation in the near-UV region (350 nm) and at long wavelengths (672 nm) is believed to be the first report of photochemical activation of functionalities at the periphery of a chlorin derivative.

Because chlorins are known to be efficient singlet oxygen sensitizers, irradiations were performed in Ar or $N_2$ saturated solutions. Irradiation of a dilute [$3\times10^{-4}$M], oxygen purged solution of 19 in benzene with 350 nm light produced a single photoproduct. Scheme 3 illustrates the expected reaction (via a diazenyl biradical intermediate, extrusion of nitrogen, and intramolecular closure of the resulting biradical as shown in Scheme 2) to form a cyclopropane (20).

Scheme 3
Formation of 20 from 19

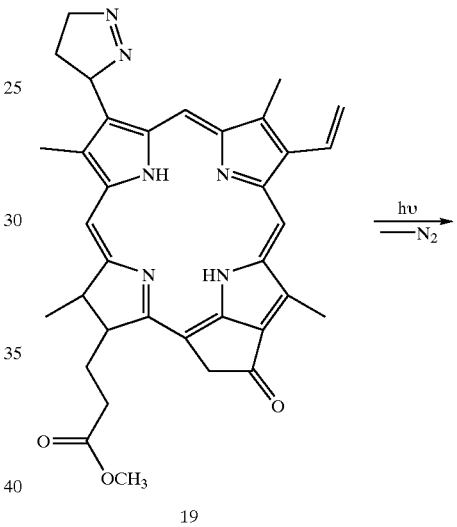

19

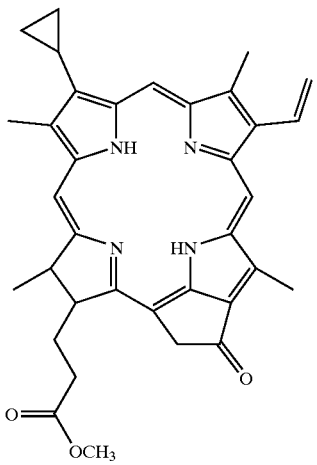

20

NMR spectroscopy, coupled with MS, and UV-vis spectroscopy data, confirms the formation and structure of the cyclopropyl photoproduct (20).

Photochemical activation of 19 by irradiation with low energy light was confirmed with use of a light emitting diode (LED) panel that emits at a single wavelength (672 nm) in the red region of the optical spectrum. Irradiation of an oxygen purged, dilute [$3\times10^{-4}$M] solution of 19 in benzene with 672 nm light produced a single photoproduct. The TLC and the spectral characteristics of this product were identical to that obtained on 350 nm excitation. Once again, this reflects unexpected photochemistry (using long wavelength activation) in part because only 43 kcal/mol of energy are produced by 672 nm light which would not be expected to initiate a reaction that involves the cleavage of a C—N covalent bond in the pyrazoline. In light of the present invention, however, any photoreactive group that can be activated by the energy of long wavelength light (from about 450 to about 750 nm) may be used in the practice of the invention. The energy of each wavelength of light can be readily determined, and photoreactive groups may be evaluated for their absorption in the above range to determine the long wavelength to use without undue experimentation.

Simple control experiments were used to confirm that the product observed was due to photochemistry and not a thermal reaction that was taking place as a result of heating by the LED. The temperature of the photoreaction was monitored by placing a thermometer in the solution to confirm that the temperature of the solution did not rise above 30° C. In comparison, after heating 19 in various solvents it was found that efficient conversion to 20 required over 42 hours of refluxing in toluene. In addition, concurrent with every photoreaction, a 'dark' reaction was carried out. A foiled vial containing the same solution as that which was irradiated was placed in front of the light source, and its products monitored. No products were ever observed from any of the dark solutions. The evidence herein suggests that photochemistry at both long (672 nm) and short (350 nm) wavelengths leads to efficient extrusion of nitrogen from the pyrazoline adduct of a polypyrrolic macrocycle to yield a cyclopropane derivative.

Without being bound by theory, it is believed that the observed photochemical reaction with long wavelength light is not the result of intramolecular energy transfer from the porphyrin to the pyrazoline because estimations indicate that it would be an extremely endothermic process. With respect to the possibility that a photoinduced electron transfer may be responsible, it is first noted that there is no precedence for this reaction with pyrazolines. If the porphyrin and pyrazoline are considered as separate molecules, however, the estimation of the feasibility of an electron transfer process may be conducted as follows. Generally, a photochemical electron transfer occurs only when it is exergonic or <5 kcal mol$^{-1}$ endergonic (Eberson, L. *Electron Transfer Reactions in Organic Chemistry*, Springer-Verlag: Berlin Germany, 1987). The free energy change for a photoinduced electron transfer can be determined from the oxidation potential of the electron donor ($E°_D$), the reduction potential of the electron acceptor ($E°_A$) and the excited state energy of the sensitizer ($E_{0,0}$), using the relationship $\Delta G_{ET}$=23.06 kcal mol$^{-1}$[($E°_D-E°_A$)-$E_{0,0}$]-C; where C is a term that accounts for solvation. In order to estimate the feasibility of electron transfer using this relationship, the redox properties of the molecules must be known. The starting materials MePPP (18), the pyrazoline (19), and the photoproduct cyclopropane (20) have reduction and oxidation potentials as shown in Table 2.

TABLE 2

Summary of redox potentials measured in dichloromethane at 22° C. versus Fc.

| Compound | Reduction 1 | Reduction 2 | Oxidation 1 |
|---|---|---|---|
| Methylpyropheophorbide (18) | −1.47 | −1.73 | 0.61 |
| Pyrazoline of MePPP (19) | −1.48 | −1.76 | 0.45 |
| Cyclopropane of MePPP (20) | −1.52 | −1.83 | 0.43 |

Figure 9:
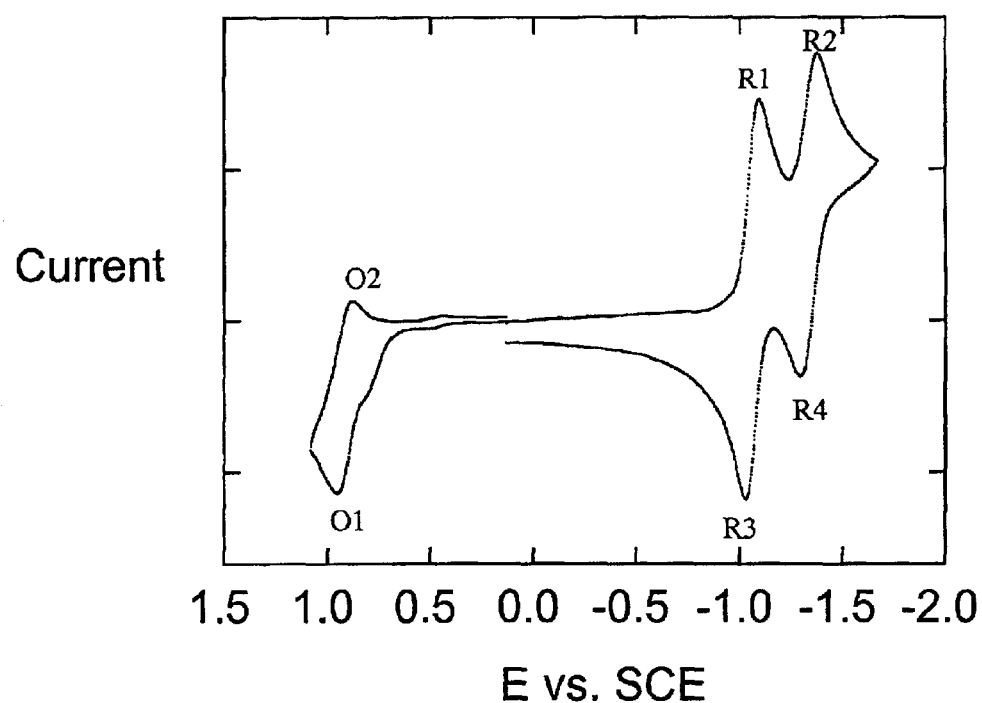
FIG. 9 depicts a cyclic voltammogram of 19 measured in methylene chloride containing 0.2M Bu$_4$NPF$_6$ on a Pt electrode at 0.2V s$^{-1}$.

FIG. 9 depicts the cyclic voltammogram of the pyrazoline which reveals the reversible nature of the reduction waves of 19 (18 and 20 are also reversible). The radical anions and dianions are therefore stable on the time scale of these experiments, with no chemistry occurring on addition of electrons to these molecules. If any chemical reactions were occurring from the radical anion or dianion, the CV's would be irreversible. The reduction potentials do not vary a great deal, indicating that these particular functionalizations of MePPP did not change the overall electronics of the molecule to a great extent. On reduction, two consecutive electrons are accepted by the porphyrin macrocycle in each of 18, 19 and 20. The oxidations are also reversible; the only notable feature of the oxidation potentials is that 19 and 20 are somewhat easier to oxidize than MePPP.

With these estimates for the reduction potential of the porphyrin from the electrochemistry and the $E_{0,0}$=1.8 eV (or 43 kcal mol$^{-1}$) available from the absorption and fluorescence data, exergonic electron transfer from the pyrazoline to the porphyrin requires the oxidation potential of the pyrazoline to be less than 0.3V. Even accounting for the solvation term, the oxidation potentials of pyrazolines are apparently too high to make electron transfer feasible in this case. Nonetheless, the electrochemical data for these compounds may be used in biological systems, where donors and acceptors are ubiquitous. When the question of whether or not electron transfer will occur between these compounds and a specified substrate, the redox information will enable the skilled practitioner to predict the outcome.

Having discussed the above theories, and without binding the invention to the following, a consideration of the entropy and enthalpy values (Boldyrev, A. I.; Schelyer, P. v. R.; Higgins, D.; Thomson, C.; Kramarenko, S. S. *Comput. Chem.* 1992, 13, 1066) highlighted the exergonicity of the reactions of the pyrazoline. It is thus theorized that upon absorption of a photon of long wavelength light, 19 forms an excited state with sufficient energy (672 nm≈43 kcal/mol) to extrude nitrogen from its pyrazoline moiety ($E_a$≈35.2 kcal/mol). While the mechanism involved in long wavelength irradiation is not known, it is reasonable to expect a mechanism similar to that invoked by the short wavelength irradiation The present invention may thus be practiced in one embodiment by selecting long wavelengths of light containing energies sufficient to form an excited state that is capable of extruding nitrogen from an azo-type photoreactive group. The excitation energies of various photoreactive groups may be calculated and/or determined experimentally.

To photoactivate photoreactive groups, the invention provides for the irradiation with long wavelength light for various times to deliver various total dosages. As appreciated by the skilled practitioner, the total dosage of light is defined as the intensity (e.g., in $mW/cm^2$)×time (e.g., in seconds) to result in energy doses (e.g. in $J/cm^2$). The invention may be practiced with various doses of light as desired, but exemplary doses are from about 0.1 to about 300, preferably from about 0.1 to 1, about 1 to 2, about 2 to 5, about 5 to 10, about 10–20, about 20–50, about 50–75, about 75–100, about 100–200, or about 200–300 $J/cm^2$.

The above discussion may also be viewed as a novel means of functionalizing porphyrins with cyclopropyl moieties. The cyclopropane ring, due to its unusual bonding and inherent ring strain (27.5 kcal/mol) is unique among carbocycles in both its properties and reactions. Thus cyclopropane derivatives are provided by the present invention as building blocks of unprecedented synthetic potential while leaving the photosensitizing macrocycle portion of the compounds intact. Moreover, natural and synthetic cyclopropanes bearing simple functionalities are endowed with a large spectrum of biological properties ranging from enzyme inhibition to antibiotic, antiviral, antitumor and neurochemical properties (Salaun, J. Topics in Current Chemistry, Vol. 207, 2000). The use of the disclosed compounds comprising a cyclopropane for the above activities is within the scope of the invention.

Administration and Use

The compounds of the invention may be used in a manner analogous to the use of any photosensitizer in photodynamic therapy (PDT). These include, but are not limited to, the diagnosis or treatment of cancer, the reduction of activated leukocytes, the treatment of ocular disorders, the treatment and prevention of neovasculature and angiogenesis, the destruction of viruses and cells infected thereby, the treatment of atherosclerotic plaques, the treatment of restenosis, and others. In addition, the compounds may be photoactivated by appropriate excitation wavelengths to fluoresce visibly. This fluorescence can then be used to localize a tumor or other target tissue.

Of course the compounds of the invention may be used singly or in combination with each other or other photosensitizers known in the art. Preferably, the compounds are administered in an effective amount such that a photodynamic effect sufficient to treat or prevent any of the diseases and conditions as disclosed herein may occur.

In addition to in vivo use, the compounds of the invention can be used in the treatment of materials in vitro to destroy harmful viruses or other infectious agents. For example, blood plasma or blood that is to be used for transfusion or banked for future transfusion, can be treated with the compounds of the invention and irradiated to effect sterilization. In addition, biological products such as Factor VIII, which are prepared from biological fluids, can be irradiated in the presence of the compounds of the invention to destroy contaminants.

The photosensitizers made from the compounds of the invention can be formulated into pharmaceutical compositions for administration to the subject or applied to an in vitro target using techniques generally known in the art. A summary of such pharmaceutical compositions may be found, for example, in Remington's Pharmaceutical Sciences, Mack Publishing Co., Easton, Pa. The compounds of the invention can be used singly or as components of mixtures. A preferred form of the compounds is as a liposomal formulation.

Generally, the compounds of the invention, labeled or unlabeled, may be administered parenterally or by injection. Injection may be intravenous, subcutaneous, intramuscular, intrathecal, or even intraperitoneal. However, the compounds may also be administered by aerosol intranasally or intrapulmonarally, or topically. Formulations designed for timed release are also with the scope of the invention. The compounds of the invention may be labeled isotopically (e.g. with a radioisotope) or by another other means, including, but not limited to, the use of chromophores or fluorescent moieties.

Injectables can be prepared in conventional forms, either as liquid solutions or suspensions, solid forms suitable for solution or suspension in a liquid prior to injection, or as emulsions. Suitable excipients are, for example, water, saline, dextrose, glycerol and the like. Of course, these compositions may also contain minor amounts of nontoxic, auxiliary substances, such as wetting or emulsifying agents, pH buffering agents, and so forth.

Systemic administration can be implemented through implantation of a slow release or sustained release system, by suppository, or, if properly formulated, orally. Formulations for these modes of administration are well known in the art, and a summary of such methods may be found, for example, in Remington's Pharmaceutical Sciences (supra).

If treatment is to be localized, such as for the treatment of superficial tumors or skin disorders, the compound can be administered topically using standard topical compositions, such as lotions, suspensions, or pastes.

The quantity of the photosensitizer compound to be administered depends upon the choice of active ingredient, the condition to be treated, the mode of administration, the individual subject, and the judgment of the practitioner. Depending on the specificity of the preparation, smaller or larger doses may be needed. For compositions that are highly specific to target tissues, such as those with a highly specific monoclonal immunoglobulin preparation or a specific receptor ligand, dosages in the range of 0.05–1 mg/kg are suggested. For compositions that are less specific to the target tissue, larger doses, up to 1–10 mg/kg may be needed. The foregoing ranges are merely suggestive, as the number of variables in regard to an individual treatment regime is large, and considerable excursions from these recommended values are not uncommon.

For activation of a photosensitizing compound of the invention, any suitable absorption wavelength is used. This can be supplied using the various methods known to the art for mediating cytotoxicity or fluorescence emission, such as visible radiation, including incandescent or fluorescent light sources or photodiodes such as light emitting diodes. Laser light can also be used for in situ delivery of light to a localized photosensitizer. In preferred embodiments of the invention, the light contains at least one wavelength in the range of about 645 to about 700 nm, more preferably from about 645 to about 650, from about 650 to about 655, from about 655 to about 660, from about 660 to about 665, from about 665 to about 670, from about 670 to about 675, from about 675 to about 680, from about 680 to about 685, from about 685 to about 690, from about 690 to about 695, and from about 695 to about 700 nm. Most preferred is light containing one or more wavelengths at 645, 650, 655, 660, 665, 670, 675, 680, 685, 690, 695, and 700 nm. In a typical protocol, for example, a compound of the invention is administered prior to irradiation.

Preferably, electromagnetic radiation containing one or more wavelength absorbed by the photosensitizing compound of the invention, such as from ultraviolet to visible and infra red light, is delivered after administration of the compound, compositions and formulations of the invention. Also preferred in the invention is the use of low-dose PDT. By "low-dose PDT", it is meant a total photodynamic therapy experience at substantially lower levels of intensity than that ordinarily employed. Generally, there are three significant variables—the concentration of the photosensitizing agent, the intensity of the radiation employed and the time of exposure to light, which determines the total amount of energy ultimately delivered to the target tissue. Generally, an increase in one of these factors permits a decrease in the others.

For example, if it is desired to irradiate only for a short period of time the energy of irradiation or the concentration of the drug may be increased. Conversely, if longer time periods of irradiation are permitted, lower irradiation intensities and lower drug concentrations are desirable. The use of low dose PDT offers an additional advantage in the form of reducing the likelihood of PDT side effects such as damage to unintended tissues.

It is understood that the manipulation of these parameters will vary according to the nature of the tissue being treated and the nature of the compound of the invention being employed. However, in general, low-dose PDT employs combinations of the drug concentration, radiation intensity, and total energy values which are several fold lower than those conventionally used for destroying target tissues such as tumors and unwanted neovascularization, including neovasculature of the eye, such as choroidal neovasculature (as associated with age related macular degeneration). One measure might be the product of photosensitizing compound concentration (e.g., in ng/ml)×intensity (e.g., in mW/cm$^2$)× time (e.g., in seconds). However, it is difficult to set absolute numbers for this product since there are constraints on each of the parameters individually. For example, if the intensity is too low, the compound will not be photoactivated consistently; if the intensity is too high, hyperthermic and other damaging effects may occur. Additionally, in some instances, ambient or environmental light available at the target cell or tissue undergoing PDT may be sufficient in the absence of additional deliberate irradiation.

Similarly, concentrations of the compound(s) of the invention cannot vary over any arbitrary range. There may also be constraints on the time during which radiation can be administered. Accordingly, the product of the foregoing equation is only a rough measure. However, this approach may provide a convenient index that can be adjusted according to the relative potency of the compound employed, and in general, an increase in intensity would permit a decrease in time of irradiation, and so forth.

Having now generally described the invention, the same will be more readily understood through reference to the following examples which are provided by way of illustration, and are not intended to be limiting of the present invention, unless specified.

EXAMPLE 1

Instrumentation and Materials

Elemental Analyses (EA)

Microanalyses were carried out in the microanalytical laboratory in the Department of Chemistry, University of British Columbia by Mr. Peter Borda using a Carlo Erba Elemental Analyzer 1106. Analysis was attempted on all pyrazoline and cyclopropyl derivatives of protoporphyrin and methylpyropheophorbide, as well as trifluoroacetyl-TPP.

Mass Spectra (MS)

Mass spectrometric analyses were carried out by the B.C. Regional Mass Spectrometry Center at the University of British Columbia, Department of Chemistry. Low and high resolution mass spectra were obtained by liquid secondary ion mass spectrometry (LSIMS), and were determined on a KRATOS Concept IIHQ hybrid mass spectrometer. Molecular ions are designated as M+.

UV-vis Spectra

UV-vis spectra were taken on a Cary 50. Wavelengths for each absorption maximum ($\lambda_{max}$) are reported in nanometers (nm), and extinction coefficients ($\epsilon(M^{-1}cm^{-1})$) are given in parentheses.

Fluorescence Instrumentation

The fluorescence measurements were performed on a SLM-AMINCO AMINCO-Bowman Series 2 Luminescence Spectrometer using a pulsed xenon lamp as the excitation source. Excitation was at 350 nm and 660 nm with a 2 nm bandwidth and emission was at 430 nm with 16 nm bandwidth. Fluorescence emissions were corrected for lamp fluctuations using the reference signal from the excitation source.

Electrochemical Studies

Cyclic Voltammetry was carried out at the University of Western Ontario, with the assistance of Prof. Mark Workentin using an E.G. & G. PAR 283 potentiostat interfaced to a personal computer using PAR 270 electrochemistry software. The electrochemical cell was maintained at 25° C. and contained 0.1 mol L-1 TEAP in 25 mL of methylene chloride purged by argon. At the beginning of every experiment the working electrode, a glassy carbon 3 mm disk, was freshly polished with 1 mm diamond paste and ultrasonically cleaned in ethanol for fifteen minutes. The counter electrode was a platinum plate and a silver wire immersed in a glass tube containing 0.1 M TEAP in the desired solvent with a fine sintered bottom was used as a quasi-reference. Ferrocene was used as an internal redox reference; the potential was calibrated against the saturated calomel electrode (SCE). To compensate for the cells internal resistance the iR compensation was adjusted to at least 95% of the oscillation value. In a typical experiment, 1 mM sample of the appropriate porphyrin was used.

Nuclear Magnetic Resonance Spectrometry (NMR)

NMR spectra were recorded either by the author, by Dr. Nick Burlinson, by Marietta Austria or Liane Darge of the University of British Columbia Chemistry Department NMR Service Laboratory.

$^1$H NMR

Proton nuclear magnetic resonance spectra ($^1$H-NMR) were recorded on the following spectrometers: Bruker WH-400 (400 MHz), Bruker AV-400 (400 MHz) and Buker AMX-500 (500 MHz). The positions of the signals are given as chemical shifts (δ) in parts per million (ppm) with respect to tetramethylsilane (TMS) at δ 0 ppm; however, the internal reference standard used in each case was the residual proton signal present in the deuterated solvent. Reported chemical shifts are followed in parentheses by the number of protons, the multiplicity of the peak, the coupling constant (J) in Hz, and the atomic assignment. The following abbreviations are used in reference to the multiplicities: s=singlet, d=doublet, t=triplet, q=quartet, dd=doublet of doublets, dt=doublet of triplets, m=multiplet, br=broad. In some cases, in order to ascertain structures, HMQC (Heteronuclear Multiple Quantum Coherence, $^1$H-$^{13}$C correlation) and NOESY (Nuclear Overhauser Effect Spectroscopy) experiments on the Bruker AMX-500 spectrometer, COSY (Correlated Spectroscopy), NOESY and homonuclear decoupling experiments on the Bruker WH-400 spectrometer were carried out.

$^{13}$C NMR

The following spectrometers were used to record the carbon nuclear magnetic resonance spectra ($^{13}$C NMR): Bruker AM-400 at 100.6 MHz, Bruker AV-300 at 74.6 MHz, and Bruker AMX-500 at 128.5 MHz. All spectra were determined with broad band proton decoupling. The position of the signals are given as chemical shifts (δ) in parts per million (ppm) with respect to tetramethylsilane at δ 0 ppm; however, the internal reference standard used in each case was the central transition of the solvent carbon atom. Reported chemical shifts are followed in parentheses by the carbon assignments, which were often made possible by an APT (attached proton test).

Crystallographic Analysis (X-ray)

The X-ray crystal structure was determined using single-crystal X-ray analysis, on a Rigaku/ADSC CCD area detector with graphite monochromated Mo-Kα radiation, and was drawn with a locally modified version of the ORTEP program at the 50% probability level. Structures were determined by Dr. Brian Patrick in the Chemistry Department of the University of British Columbia.

Chromatography

Chromatographic purifications of compounds were carried out using silica gel 60, 70–230 mesh, supplied by E. Merck Co. Thin layer chromatography (TLC) was carried out on pre-coated silica gel plates (Merck 60, 230–400 mesh, with aluminum backing and fluorescent indicator ($F_{254}$). Preparative thin layer chromatography was prepared on pre-coated 10×10 cm 0.5 or 1 mm thick Whatman or Merck silica gel plates.

Preparative thin layer chromatography was also carried out using the Chromatotron®, when necessary, whereby circular plates of Merck 60, 230–400 mesh with fluorescent indicator ($F_{254}$) were prepared on site.

Reaction Conditions

Due to the inherent light sensitivity of these compounds, all reactions were performed in a blacked-out fume hood or surrounded by aluminum foil.

Reagents and Solvents

Unless otherwise specified, reagents were used as supplied by the Aldrich Chemical Company. Solvents were reagent or HPLC grade and purified using standard literature methods when necessary. Deuterated solvents were supplied by Cambridge Isotope Laboratory.

EXAMPLE 2

Photochemical Studies—General Procedures

Irradiation Sources

Photochemical irradiations were carried out with either a 250W Osram HLX 64655 arc lamp in an Oriel lamp housing, a Rayonet Photochemical Chamber Reactor (Model RPR-100) or a 672 nm Light Emitting Diode. The light output from the Oriel lamp passed through a glass filter: P70-600-S-533G-Corion Solution State Irradiation Spectral-grade solvents were used for irradiations. For preparative-scale irradiations, the solution of the substrate in the appropriate solvent was placed in a 50 mL septum-sealed tube and deoxygenated with nitrogen or argon for 30 minutes, with stirring, prior to reaction. Efficient stirring was maintained throughout the irradiation period when possible. For irradiations carried out with the Osram lamp and the LED, the substrate was placed 6–10 cm from the source, and supported on a retort stand. In the case of the Rayonet Reactor, the tubes were suspended by copper wire in the chamber and were not stirred during irradiation.

Analysis of Photochemical Reactions

The photochemical reactions were monitored by thin layer chromatography. To insure exclusion of oxygen, these were purged with nitrogen or argon, a large needle was inserted through the septum and aliquots were removed with a capillary. In some cases UV-vis spectrometry was also performed on these aliquots.

EXAMPLE 3

Preparation of Protoporphyrin Pyrazolines 8, 9 and 10

The pyrazolines of protoporphyrin-dimethylester were synthesized according to a modified procedure for the reactions of diazomethane reported by Black (*Aldrichimica Acta* 1983, 16, 3–10.). A diazomethane apparatus appropriate for production of (1–50 mmol) of diazomethane was used. First, the cold finger was filled with acetone and dry ice. A solution of potassium hydroxide (13.36 g, 0.238 mol) in water (20 ml) was then added to the reaction vessel, followed by ethanol (10 ml). A 60 ml separation funnel was then placed over the reaction vessel, sealed and supported by a rubber septum that had a whole bored through it. The 100 ml receiver flask containing PP-DME (7) (0.5 g, 0.846 mol) in a minimum amount of methylene chloride and a stir bar was placed under the condenser, and cooled in an ice bath. An ether trap was not used. The separation funnel was then charged with diazald (12.74 g, 0.59 mol) in a minimum amount of diethylether (~40 mls). Solutions may be sonicated to facilitate dissolution. The reaction vessel was heated to 60° in a water bath, and the apparatus was kept behind a blast shield from this point on. Diazald in ether was slowly added to the reaction vessel via the separation funnel, at a rate attempting to match that of the formation of yellow diazomethane gas apparent on the condenser. Once the addition was complete, the separation funnel was flushed with a minimum amount of ether, to dissolve residual amounts of diazald.

A 'diazo-balloon' was then attached to the top of the receiver flask, and placed behind the blast shield or in a canister, left to stir in the dark, overnight. The reaction was followed by thin layer chromatography using only makeshift plastic capillaries to remove aliquots (any sharp edges solicit the risk of detonation of diazomethane). In the event the reaction had not proceeded to completion, the solvent (and diazomethane) were evaporated and the reaction mixture re-exposed to the aforementioned diazomethane procedure. The use of the 'diazo-balloon' greatly reduced the need for re-exposure.)

After satisfactory conversion, the reaction was quenched by removal of solvent and diazomethane-carrying ether (usually in fume hood, under a gentle stream of nitrogen.) Separation of the three pyrazoline products was only effective using the Chromatotron, starting 100% methylene chloride to introduce the product mixture to the circular silica plate, and increasing the polarity thereafter (0.5%→5% THF in $CH_2Cl_2$ eluent). The recovered yield of the three products was 78%, in a ratio of 1(8):1(9):2(10). Recovered starting material accounted for a remaining 20%.

EXAMPLE 4

Spectroscopic Data for Compounds 8, 9 and 10

Compound 8

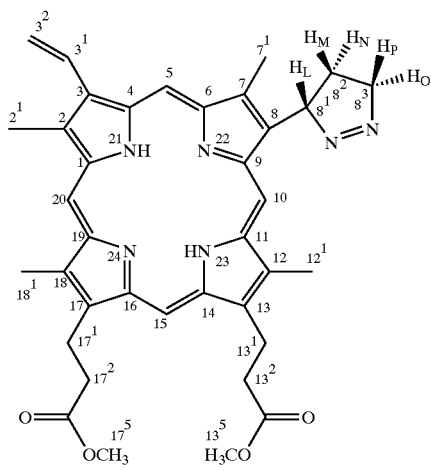

EA: Calculated for $C_{37}H_{40}N_6O_4$: C, 70.23; H, 6.37; N, 13.28. Found C, 69.85; H, 6.39; N,12.57

MS LR+LSIMS (matrix: thioglycerol): Exact mass calculated for $C_{37}H_{40}N_6O_4$ (M+1): 633.75. Found 633.

MS HR+LSIMS (matrix: thioglycerol): Found C, 37; H, 41; O, 4; N, 6 (M+1) 633.31948, (dev 0.87).

$^1$H NMR (400 MHz, $CDCl_3$): δ 9.94 (1H, s, H-5), 9.91 (1H, s, H-20), 9.83 (1H, s, H-15), 9.61 (1H, s, H-10), 8.14 (1H, m, $J_{trans}$=17.8, $J_{cis}$=11.5, H-3$^1$), 6.80 (1H, m, $J_{L-M,}$ $_{L-N}$=9.7, $J_{L-O,}$ $_{L-P}$=2.5, $H_L$-8$^1$), 6.29 (1H, m, $J_{tans}$=17.9, $J_{gem}$=1.3, H-3$^2$), 6.13 (1H, m, $J_{cis}$=11.5, $J_{gem}$=1.3, H-3$^2$), 5.45 (1H, m, $J_{O—P}$=17.8, $J_{O—M}$=9.8, $J_{O-N,}$ $_{O-L}$=2.7, $H_O$-8$^3$), 4.74 (1H, m, $J_{P-O}$=18.4, $J_{P-M,}$ $_{P—N}$=9.4, $J_{P—L}$=2.8, $H_P$-8$^3$), 4.28 (2H, t, J=7.5, H-13$^1$), 4.27 (2H, t, J=7.5, H-17$^1$), 3.65 (3H, s, H-13$^5$), 3.64 (3H, s, H-17$^5$), 3.54 (3H, s, H-12$^1$), 3.51 (3H, s, H-18$^1$), 3.48 (3H, s, H-7$^1$), 3.47 (3H, s, H-2$^1$) 3.21 (2H, t, J=7.7, H-13$^2$), 3.20 (2H, t, J=7.7, H-17$^2$), 2.74 (1H, m, $J_{M-N}$=22.4, $J_{M-P}$=9.7, $J_{M-L}$=3.1, $H_M$-8$^2$), 2.11 (1H, m, $J_{N-M}$=22.7, $J_{N-L,}$ $_{N—P}$=9.7, $J_{N-O}$=3.2, $H_N$-8$^2$), −3.72 (2H, s, NH)

UV-VIS ($CH_2Cl_2$) $λ_{max}$ (rel. intensity): 406 (1), 502 (0.08), 536 (0.06), 572 (0.05), 626 (0.02)

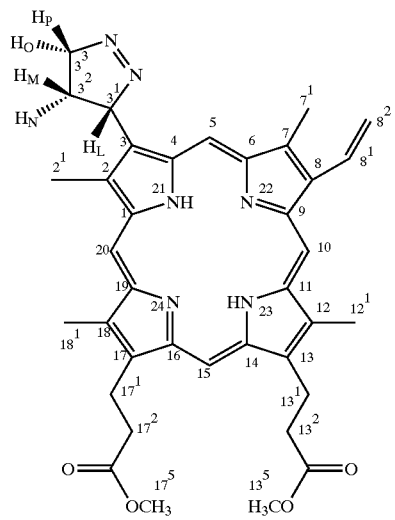

EA: Calculated for $C_{37}H_{40}N_6O_4$: C, 70.23; H, 6.37; N, 13.28. Found C, 69.88; H, 6.34; N, 12.58

MS LR+LSIMS (matrix: thioglycerol): Exact mass calculated for $C_{37}H_{40}N_6O_4$ (M+1): 633.75. Found 633.

MS HR+LSIMS (matrix: thioglycerol): Found C, 37; H, 41; O, 4; N, 6 (M+1) 633.31937, (dev 0.69).

$^1$H NMR (400 MHz, $CDCl_3$): δ 9.95 (1H, s, H-10), 9.79 (1H, s, H-15), 9.69 (1H, s, H-20), 9.57 (1H, s, H-5), 8.05 (1H, m, $J_{rans}$=17.8, $J_{cis}$=11.5, H-8$^1$), 6.81 (1H, m, $J_{L-M,}$ $_{L-N}$=9.8, $J_{L-O,}$ $_{L-P}$=2.6, $H_L$-3$^1$), 6.23 (1H, m, $J_{trans}$=17.8, $J_{gem}$=1.2, H-8$^2$), 6.10 (1H, m, $J_{cis}$=11.5, $J_{gem}$=1.2, H-8$^2$), 5.46 (1H, m, $J_{O—P}$=17.9, $J_{O-M}$=9.8, $J_{O-N,}$ $_{O-L}$=2.6, $H_O$-3$^3$), 4.75 (1H, m, $J_{P-O}$=17.9, $J_{P-M,}$ $_{P-N}$=9.3, $J_{P-L}$=2.8, $H_P$-3$^3$), 4.28 (2H, t, J=7.8, H-13$^1$), 4.24 (2H, t, J=7.8, H-17$^1$), 3.36 (3H, s, H-13$^5$), 3.65 (3H, s, H-17$^5$), 3.49 (3H, s, H-7$^1$), 3.46 (3H, s, H-2$^1$), 3.43 (3H, s, H-12$^1$), 3.42 (3H, s, H-18$^1$), 3.21 (2H, t, J=7.8, H-13$^2$), 3.18 (2H, t, J=7.8, H-17$^2$), 2.72 (1H, m, $J_{M-N}$=13.0, $H_M$-3$^2$), 2.10 (1H, m, $J_{M-N}$=13.0, $H_N$-3$^2$), −4.20 (2H, s, NH)

$^{13}$C NMR (125.8 MHz, $CDCl_3$) (quaternary carbons are unresolved, C=19): δ 97.62, 96.86, 96.66, 95.89, 129.99, 85.89, 120.57, 77.81, 21.65, 21.62, 51.69, 51.67, 11.42, 12.41, 11.83, 11.51, 36.79 (2×C), 27.72.

UV-VIS ($CH_2Cl_2$) $λ_{max}$ (rel. intensity): 404 (1), 502 (0.08), 536 (0.06), 572 (0.05), 626 (0.02)

Compound 10

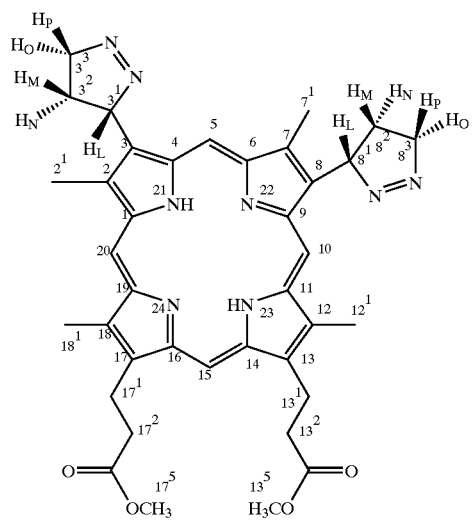

EA: Calculated for $C_{38}H_{42}N_8O_4$: C, 67.64; H, 6.27; N, 16.61. Found C, 67.50; H, 6.26; N, 15.60

MS LR+LSIMS (matrix: thioglycerol): Exact mass calculated for $C_{38}H_{42}N_8O_4$ (M+1): 675.79. Found 675.

MS HR+LSIMS (matrix: thioglycerol): Found C, 38; H, 43; O, 4; N, 8 (M+1) 675.33975, (dev −1.45).

$^1$H NMR (400MHz, CDCl$_3$): δ 10.08 (1H, s, H-20), 10.03 (1H, s, H-15), 9.81, 9.79 (1H, s, H-5) 9.73, 9.71 (1H, S, H-10), 6.91 (2H, m, H$_L$-3$^1$, 8$^1$), 5.55, 5.50 (2H, m, J$_{O-P}$= 17.9, J$_{O-M}$=10.0, J$_{O-N, O-L}$=2.5, H$_O$-3$^3$, 8$^3$), 4.82, 4.78 (2H, m, H$_P$-3$^3$, 8$^3$), 4.37 (2H, t, J=7.4, H-13$^1$), 4.36 (2H, t, J=7.4, H-17$^1$), 3.64 (3H, s, H-13$^5$), 3.64 (3H, s, H-17$^5$), 3.60 (3H, s, H-18$^1$), 3.56, 3.55 (3H, s, H-7$^1$), 3.54, 3.53 (3H, s, H-12$^1$), 3.50, 3.49 (3H, s, H-2$^1$), 3.26 (2H, t, J=7.7, H-13$^2$), 3.25 (2H, t, J=7.7, H-17$^2$), 2.84 (2H, m, H$_M$-3$^2$, 8$^2$), 2.24, 2.22 (2H, m, H$_N$-3$^2$, 8$^2$), −3.75 (2H, s, NH)

UV-VIS (CH$_2$Cl$_2$) λ$_{max}$ (rel. intensity): 400 (1), 500 (0.10), 534 (0.07), 570 (0.05), 622 (0.03)

EXAMPLE 5

Photoproducts of Protoporphyrin Pyrazolines (15), (16), and (17)

Stirred, deoxygenated solutions of each of the pyrazolines of protoporphyrin-dimethylester in benzene were irradiated in the Rayonet reactor (35 Å bulbs) and with red-filtered light (Corion 600). The following Table 3 outlines the solution concentrations, irradiation times, and isolated product yield:

TABLE 3

| | Conc. (g/mL), mmol | Time (h) | Product yield (%) |
|---|---|---|---|
| Rayonet Photochemical Chamber Reactor | | | |
| A-ring pyrazoline | 3.06 × 10$^{-4}$, 0.017 | 22.5 | 82.4 |
| B-ring pyrazoline | 5.00 × 10$^{-3}$, 0.016 | 21 | 52.4 |
| Di-adduct pyrazoline | 2.29 × 10$^{-4}$, 0.014 | 5 | 50.0 |
| 650 nm filtered light | | | |
| A-ring pyrazoline | 8.00 × 10$^{-5}$, 0.006 | 14 | 35.3 |
| B-ring pyrazoline | 2.40 × 10$^{-4}$, 0.019 | 7 | 52.3 |
| Di-adduct pyrazoline | 2.60 × 10$^{-4}$, 0.019 | 38 | 78.5 |

Benzene was removed in vacuo, and the residue dissolved in dichloromethane. The crude compounds were chromatographed on silica gel 60, 70–230 mesh, 3%–10% EtAce/CH$_2$Cl$_2$ gradient eluent). The appropriate fractions were pooled and evaporated to give the respective yields of the desired cyclopropyl derivatives. A large proportion of the starting material was recovered in each case, which accounts for the incomplete conversion to products.

EXAMPLE 6

Spectroscopic Data for Compounds 15, 16 and 17

Compound 15

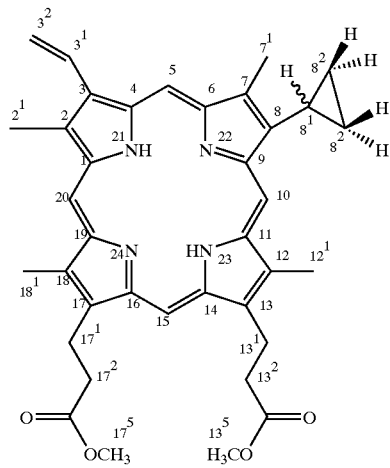

MS LR+LSIMS (matrix: thioglycerol): Exact mass calculated for $C_{37}H_{40}N_4O_4$ (M+1): 605.747. Found 605.

MS HR+LSIMS (matrix: thioglycerol): Found C, 37; H, 40; O, 4; N, 4 (M+1) 605.31293, (dev 0.24).

$^1$H NMR (400 MHz, CDCl$_3$): δ 10.44 (1H, s, H-5), 10.16 (1H, s, H-20), 10.01 (1H, s, H-15), 10.00 (1H, s, H-10), 8.28 (1H, m, J$_{trans}$17.8, J$_{cis}$=11.5, H-3$^1$), 6.35 (1H, m, J$_{trans}$=17.7, J$_{gem}$=1.4, H-3$^2$), 6.15 (1H, m. J$_{cis}$=11.5, J$_{gem}$=1.4, H-3$^2$), 4.40 (2H, t, J=7.6, H-13$^1$), 4.36 (2H, t, J=7.6, H-17$^1$), 3.71

(3H, s, H-12¹) 3.68 (3H, s, H-18¹), 3.65 (3H, s, H-13⁵), 3.65 (3H, s, H-17⁵), 3.62 (3H, s, H-7¹), 3.59 (3H, s, H-2¹), 3.27 (2H, t, J=7.9, H-13²), 3.26 (2H, t, J=7.8, H-17²), 3.05 (1H, m, $J_{doub}$=8.2, $J_{doub}$=8.2, H-8¹), 1.67 (2H, m, H-8²), 1.46 (2H, m, H-8²), −3.76 (2H, s, NH)

UV-VIS (CH₂Cl₂) $\lambda_{max}$ (rel. intensity): 402 (1), 502 (0.08), 538 (0.07), 572 (0.04), 626 (0.02)

Compound 16

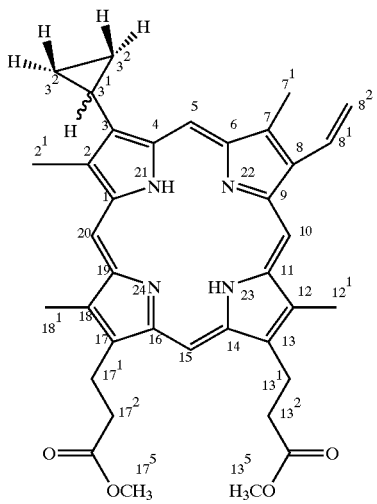

16

EA: Calculated for $C_{37}H_{40}N_4O_4$: C, 73.49, H, 6.67; N, 9.26. Found C, 72.02; H, 6.88; N, 7.93

MS LR+LSIMS (matrix: thioglycerol): Exact mass calculated for $C_{37}H_{40}N_4O_4$ (M+1): 605.747. Found 605.

MS HR+LSIMS (matrix: thioglycerol): Found C, 37; H, 41; O, 4; N, 4 (M+1) 605.31293, (dev 0.24).

¹H NMR (400 MHz, CDCl₃): δ 10.38 (1H, s, H-10), 10.14 (1H, s, H-15), 10.07 (1H, s, H-20), 10.02 (1H, s, H-5), 8.28 (1H, m, $J_{trans}$=17.6, $J_{cis}$=11.4, H-8¹), 6.33 (1H, m, $J_{trans}$=17.7, $J_{gem}$=1.4, H-8²), 6.14 (1H, m, $J_{cis}$=11.5, $J_{gem}$=1.4, H-8²), 4.40 (2H, t, J=7.7, H-13¹), 4.37 (2H, t, J=7.8, H-17¹), 3.68 (3H, s, H-12¹), 3.67 (3H, s, H-18¹), 3.64 (3H, s, H-17¹), 3.63 (3H, s, H-13⁵), 3.63 (3H, s, H-17⁵), 3.61 (3H, s, H-2¹), 3.26 (2H, t, J=7.7, H-13²), 3.26 (2H, t, J=7.6, H-17²), 3.06 (1H, m, $J_{doub}$=7.6, $J_{doub}$=7.6, H-3¹), 1.66 (2H, m, $J_{(?)}$=2.0, H-3²), 1.45 (2H, m, $J_{(?)}$=1.7, H-3²), −3.75 (2H, s, NH)

UV-VIS (CH₂Cl₂) $\lambda_{max}$ (rel. intensity): 404 (1), 502 (0.07), 538 (0.06), 572 (0.05), 626 (0.03)

Compound 17

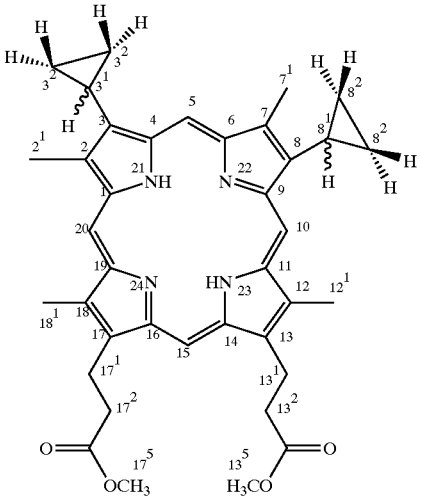

17

EA: Calculated for $C_{38}H_{42}N_4O_4$: C, 73.76, H, 6.84; N, 9.05. Found C, 73.66; H, 7.54; N, 7.11

MS LR+LSIMS (matrix: thioglycerol): Exact mass calculated for $C_{38}H_{42}N_4O_4$ (M+1): 619.747. Found 619.

MS HR+LSIMS (matrix: thioglycerol): Found C, 38; H, 43; O, 4; N, 4 (M+1) 619.32852, (dev 0.15).

¹H NMR (400 MHz, CDCl₃): δ 10.41 (1H, s, H-10), 10.39 (1H, s, H-15), 10.04 (1H, s, H-20), 10.02 (1H, s, H-5), 4.41 (2H, t, J=7.7, H-13¹), 4.39 (2H, t, J=7.8, H-17¹), 3.68 (3H, s, H12¹), 3.67 (3H, s, H-18¹), 3.64 (3H, s, H-17¹), 3.63 (3H, s, H-13⁵), 3.63 (3H, s, H-2¹), 3.26 (2H, t, J=7.7, H-13²), 3.27 (2H, t, J=7.6, H-17²), 3.05 (1H, m, H-3¹ and H-8¹), 1.66 (4H, m, $J_{(vic)}$=1.9, H-3² and H-8²), 1.45 (4H, m, $J_{(?)}$=1.5, H-3² and H-8²), −3.74 (2H, s, NH)

UV-VIS (CH₂Cl₂) $\lambda_{max}$ (rel. intensity): 400 (1), 500 (0.09), 534 (0.07), 568 (0.05), 622 (0.04)

EXAMPLE 7

Preparation of Methylpyropheophorbide Pyrazoline (19)

The pyrazoline of methylpyropheophorbide was synthesized according to a modified procedure for the reactions of diazomethane reported by Black (see above). In most cases, this reaction was carried out immediately following the addition of diazomethane to protoporphyrin-dimethylester. Thus, enough potassium hydroxide was added to the reaction vessel to accommodate the formation of diazomethane for both reactions. The portion of the aqueous solution required for this reaction was (2.88 g, 0.051 mol) of potassium hydroxide, followed by addition of ethanol (10 mls). The separation funnel was then charged with diazald (2.75 g, 0.013 mol) in a minimum amount of diethylether. Upon formation, the diazomethane was delivered to a 50 ml receiver flask containing methylpyropheo-phorbide(0.5 g, 0.911 mol) in a minimum amount of methylene chloride. The reaction was then left to stir overnight.

The crude compound was chromatographed on silica gel 60, 70–230 mesh, 2%–10% EtAce/CH₂Cl₂ gradient eluent). The appropriate fractions were pooled and evaporated to yield 0.419 g (78% yield) of the desired pyrazoline. 15% of the starting material did not react, and was recovered.

19

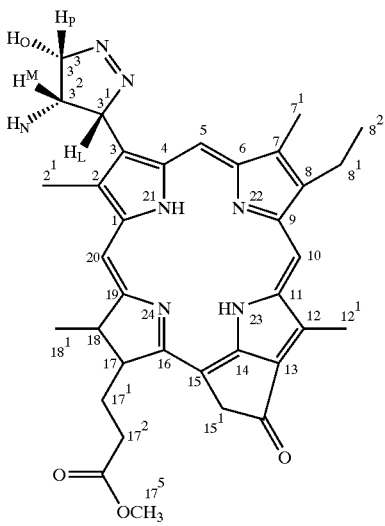

EA: Calculated for C$_{35}$H$_{38}$N$_6$O$_3$: C, 71.16, H. 6.48; N. 14.23. Found C, 70.72; H, 6.72; N, 13.63

MS LR+LSIMS (matrix: thioglycerol): Exact mass calculated for C$_{35}$H$_{38}$N$_6$O$_3$ (M+1): 591.73. Found 591.

MS HR+LSIMS (matrix: thioglycerol): Found C, 35; H, 39; O, 3; N, 6 (M+1) 591.30823, (dev −0.23).

$^1$H NMR (400 MHz, CDCl$_3$): δ 9.51 (1H, s, H-10), 8.96 (1H, s, H-20), 8.57 (1H, s, H-5), 6.67 (1H, m, J$_{L-M, L—N}$=9.7, J$_{L-O, L—P}$=2.2, H$_L$-3$^1$), 5.47 (1H, m, J$_{O-P}$=17.6, J$_{O-M}$=10.1, J$_{O-N, O-L}$=2.5, H$_O$-3$^3$), 5.26 (1H, d, J=19.6, H-15$^1$), 5.11 (1H, d, J=19.6, H-15$^1$), 4.76 (1H, m, J$_{P-O}$=18.2, J$_{P-M, P-N}$=9.1, J$_{P-L}$=3.1, H$_P$-3$^3$), 4.48 (1H, m, J$_{doub}$=7.4, J$_{quart}$=7.1, H-18), 4.29 (1H, m, J$_{doub}$=8.1, J$_{doub}$=2.2, J$_{doub}$=2.2, H-17), 3.68 (2H, t, J=7.4, H-17$^2$), 3.65 (3H, s, H-17$^5$), 3.59 (3H, s, H-7$^1$), 3.25 (3H, s, H-2$^1$), 3.17 (3H, s, H-12$^1$), 2.75 (1H, m, J$_{M—N}$=19.7, J$_{M-P}$=7.6, J$_{M-O, M-L}$=2.4, H$_M$-3$^2$), 2.68 (1H, m, H-17$^1$), 2.55 (1H, m, H-8$^1$), 2.28 (1H, m, H8$^1$), 2.28 (1H, m, H-17$^1$), 2.11 (1H, m, J$_{N-M}$=19.6, J$_{N-L, N—O}$=9.7, H$_N$-3$^2$), 1.80 (3H, d, J=7.4, H-18$^1$), 1.67 (3H, t, J=7.7, H-8$^2$), −1.77 (2H, s, NH)

$^{13}$C NMR (125.8 MHz, CDCl$_3$) (total C=35) 210.68, 195.67, 71.28, 160.45, 154.72, 150.91, 148.92, 144.99, 141.05, 137.95, 135.96, 135.33, 134.66, 132.81, 130.62, 128.56, 106.28, 104.08, 96.69, 93.01, 85.32, 78.01, 51.75, 51.61, 50.01, 48.01, 30.93, 29.85, 27.32, 23.10, 19.38, 17.33, 11.94, 11.45, 11.11

UV-VIS (CH$_2$Cl$_2$) λ$_{max}$: 411.0 (107, 100), 506.4 (10, 800), 536.5 (9, 500), 608.0 (8, 070), 663.5 (46, 061)

EXAMPLE 8

Photoproduct of Methylpyropheophorbide Pyrazoline (20)

A stirred, deoxygenated solution of the pyrazoline of methylpyropheophorbide in benzene (2.75×10$^{-4}$ g/mL, 0.023 mmol) was irradiated in front of a 672 nm LED panel for 14 hours. Thin layer chromatography revealed completion of the reaction, and benzene was removed in vacuo. The residue was dissolved in dichloromethane, and the crude compound was chromatographed on silica gel 60, 70–230 mesh, 3%–10% EtAce/CH$_2$Cl$_2$ gradient eluent). The appropriate fractions were pooled and evaporated to give (0.0130 g, 0.023 mmol, 98.6%) the cyclopropane derivative of methylpyropheophorbide.

20

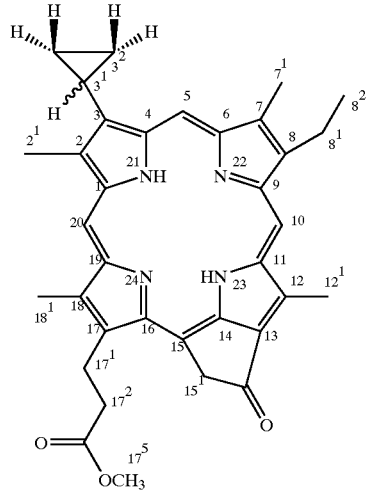

MS LR+LSIMS (matrix: thioglycerol): Exact mass calculated for C$_{35}$H$_{38}$N$_4$O$_3$ (M+1): 563.712. Found 563.

$^1$H NMR (400 MHz, CDCl$_3$): δ 9.55 (1H, s, H-10), 9.46 (1H, s, H-20), 8.41 (1H, s, H-5), 5.22 (1H, d, J=19.6, H-15$^1$), 5.10 (1H, d, J=19.6, H-15$^1$), 4.43 (1H, m, J$_{doub}$=7.4, J$_{quart}$= 7.1, H-18), 4.24 (1H, m, J$_{doub}$=8.5, J$_{doub}$=2.2, J$_{doub}$=2.2, H-17), 3.68 (2H, t, J=7.6, H-17$^2$), 3.64 (3H, s, H-17$^5$), 3.58 (3H, s, H-7$^1$), 3.35 (3H, s, H-2$^1$), 3.24 (3H, s, H-12$^1$), 2.80 (1H, t, H-3$^1$), 2.67 (1H, m, H-17$^1$), 2.52 (1H, m, H-8$^1$), 2.30 (1H, m, H-17$^1$), 2.27 (1H, m, H-8$^1$), 1.77 (3H, d, J=7.3, H-18$^1$), 1.68 (3H, t, J=7.8, H-8$^2$), 1.57 (2H, m, J=1.9, H-3$^2$), 1.30 (2H, m, J=1.6, H-3$^2$), −1.65 (2H, s, NH)

UV-VIS (CH$_2$Cl$_2$) λ$_{max}$: 410.5 (112,000), 505 (9,800), 536 (9,200), 603 (8,400), 658 (46,400)

EXAMPLE 9

Derivatives of Tetraphenylporphyrin TPP

The present invention also provides for novel derivatives of tetraphenylporphyrin (TPP) and diphenylporphyrin (DPP), including novel derivatives comprising fluorine atoms. TPP is simple and inexpensive to prepare. The present invention provides for the derivatization of TPP as part of the synthesis of diazirine TPP as shown in Scheme 4 below.

A point of interest regarding these compounds is the presence of fluorine atoms. In porphyrin and chlorin systems, it has been shown that overall lipophilicity of the molecules plays an important role in PDT efficacy. Coupled with the interesting solubility properties brought about by the incorporation of fluorine functionalities, $^{19}$F NMR can be used to provide the pharmacokinetic profiles of these photosensitizers, thus greatly increasing the ability to study mechanistic aspects of in vivo photodynamic therapy (Li, G.; Chen, Y.; Missert, J. R.; Rungta, A.; Dougherty, T. J.; Grossman, Z. D.; Pandey, R. K. J. Chem. Soc., Perkin Trans 1, 1999, 1785–1787).

Scheme 4

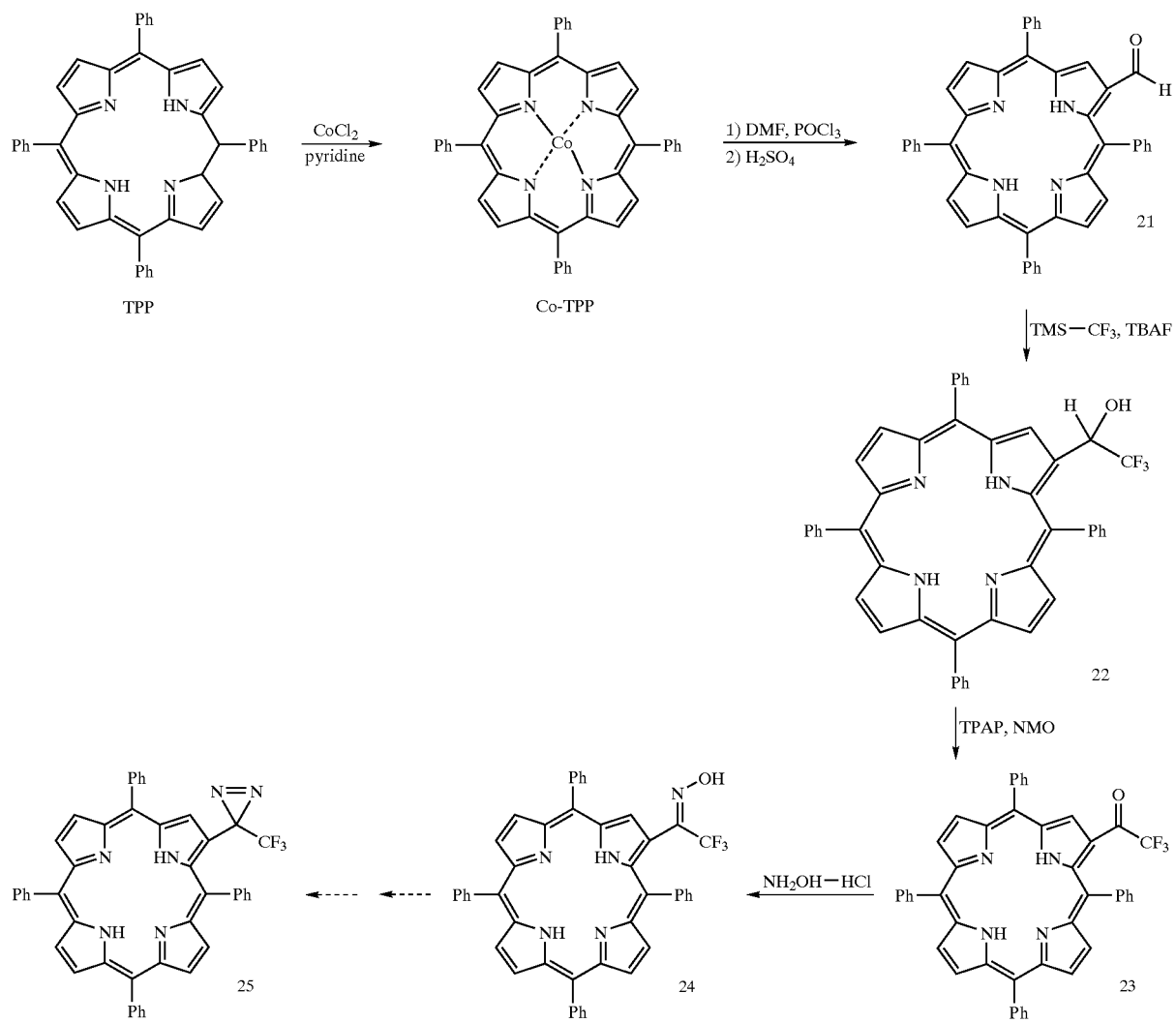

The reactions in Scheme 4 are based on a combination of two published synthetic strategies. The transformations that lead to the trifluoroacetyl-TPP (23) are based on a modified procedure by Ravindra Pandey, who worked on octaethylporphyrin and functionalized it at he meso position. From the trifluoroacetyl towards the diazirine, the reactions are planned according to a series of reactions that have previously been carried out on aryl systems (Hiberty, P. C.; Jean, V. *J. Am. Chem. Soc.* 1979, 101, 2538).

The methodology is believed to be the first example of the utility of the trimethylsilyltrifluoromethyl (TMSCF$_3$) reagent for introducing a trifluoromethyl group at the β-position of a porphyrin macrocycle. The electron withdrawing groups most commonly employed at the meso positions of the porphyrins are the perhalophenyls and perfluoalkyl groups obtained by total synthesis (Wijesekera, T. P.; Dolphin, D. in *Metalloporphyrins in Catalytic Oxidations*, ed. Sheldon, R.; Dekker, M., New York, 1994, 193–239). In addition, the reaction of porphyrin (22) (obtained by treating the related formyl analog with TMSCF$_3$), with tetrapropyl ammonium perruthenate (TPAP)-N-methyl-morpholine N-oxide (NMO) is believed to be the first example of introducing the trifluoroacetyl group at the β-position of the porphyrin system 23.

Formyl-tetraphenylporphyrin (21)

Formyl-tetraphenylporphyrin (21) was synthesized according to a modification of the procedure reported by Ponomarev et al. (*Chemistry of Heterocyclic Compounds* 1982, 18, 50). A solution of CoTPP (500 mg, 0.744 mmol) in dichloroethane (300 mL) was added to a pre-formed Vilsmeier complex (dimethylformamide: 1.9 mL, 1.79 g, 24.52 mmol and phosphorusoxychloride: 2.25 mL, 3.70 g, 24.14 mmol) in a 2 L RBF and heated at 60° C. for 30 minutes.

The solvent was then evaporated in vacuo, and 500 mL of cold water added rapidly to the oily residue. After 10 minutes, the precipitate was removed by water aspirator filtration through a coarse sintered glass filter and left to air dry overnight. The resultant crude salt, a dark green powder, was used in the following steps without purification.

The immonium salt, having been returned to the 2 L flask, was then dissolved in 10–15 mL of concentrated sulfuric acid and stirred for 1 hour. 300 mL of benzene and then a maximum amount saturated sodium acetate solution were added and left to reflux for an hour. Upon cooling, the organic layer was separated and the aqueous layer checked for neutrality. In the event the product was not yet neutralized, the separation funnel was charged with additional sodium acetate solution. The organic layer was passed through cotton and evaporated to dryness. The solvent was removed by evaporation and the residue chromatographed on silica gel 60, 70–230 mesh, 50–100% $CH_2Cl_2$/hexanes as gradient eluent). Of the four bands apparent, the fastest moving, peach coloured band accounted for a small proportion of unreacted CoTPP ($R_f$=0.8). The dark green band ($R_f$=0.5) was the desired product, and two lighter green bands ($R_f$=0.3, $R_f$=0.24) are yet undefined because their presence is so slight. The appropriate fractions were pooled and dried to afford 0.232 g (49%) of the desired purple crystals, formyl-tetraphenyl porphyrin.

mL) was added TMS-$CF_3$ (1.16 μL, 0.585 mmol). The mixture was cooled to 0° under argon, and a catalytic amount of TBAF (10 μL, 0.01 mmol) was added. The reaction was monitored by TLC whereby disappearance of the green starting material ($R_f$=0.5) and appearance of the reddish, faster moving trifluoromethylated siloxy intermediate ($R_f$=0.78) signaled completion of the reaction. Hydrolysis was achieved by addition of 0.5M hydrochloric acid (until the solution takes on a bright green colour). Methylene chloride and a solution of saturated sodium acetate were then added to neutralize the product. The organic layer was separated, the solvent removed in vacuo, and the residue chromatographed on silica gel 60, 70–230 mesh, (50–100% $CH_2Cl_2$/hexanes as gradient eluent) to yield 24.7 mgs (89%) of trifaoromethanol-tetraphenylporphyrin. One faint impurity was visible by TLC, a light green spot ($R_f$=0.73), but did not impede isolation of the desired product ($R_f$=0.34) which moved much slower.

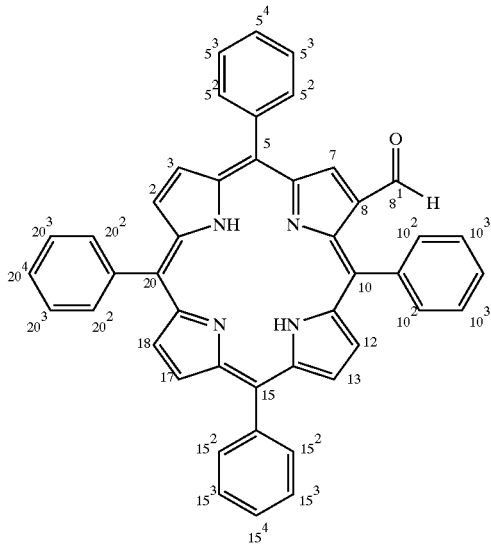

21

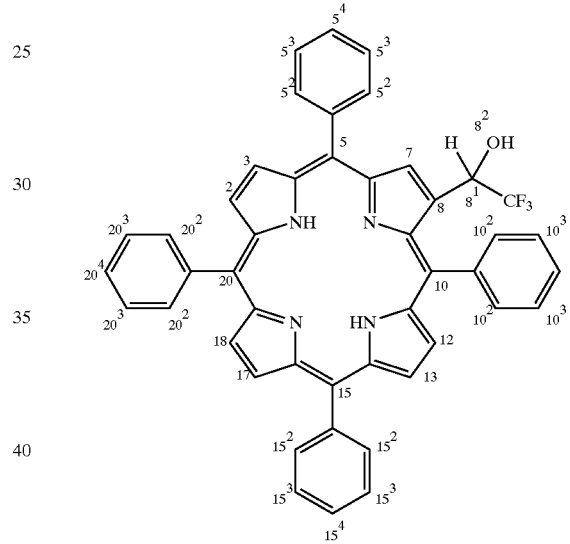

22

MS LR+LSIMS (matrix: thioglycerol): Exact mass calculated for $C_{45}H_{30}N_4O_3$ (M+1): 699.42. Found 699.

$^1$H NMR (300 MHz, $CDCl_3$): δ 9.46 (1H, s, H-8$^1$), 9.24 (1H, s, H-7), 8.92 (4H, 8.82 (2H, s, H-17,18), 8.23 (8H, m, H-5$^2$, 10$^2$, 15$^2$, 20$^2$), 7.77 (12H, m, H-5$^{3,4}$, 10$^{3,4}$, 15$^{3,4}$, 20$^{3,4}$)

$^{13}$C NMR (75 MHz, $CDCl_3$) (quaternary carbons are unresolved, C=28): δ 189.26, 142.43, 141.76, 141.57, 134.98, 134.63, 134.58, 134.55, 134.55, 133.34, 133.32, 130.79, 130.05, 130.03, 128.98, 128.14, 127.92, 127.92, 127.36, 127.36, 126.84, 126.84, 126.84, 126.81, 122.60, 120.59, 120.28, 120.00.

UV-VIS ($CH_2Cl_2$) $\lambda_{max}$ (rel. intensity): 430.9 (1), 466, (0.06), 526.0 (0.07), 567.0 (0.03), 606.0 (0.03), 662.0 (0.03)

Trifluoromethanol-tetraphenylporphyrin (22)

Trifluoromethanol-tetraphenylporphyrin (22) was synthesized according to a modification of the procedure reported by Prakash and Olah (J. Am. Chem. Soc. 1989, 111, 393). All flasks and syringes were flame-dried and cooled under argon. To a stirring solution of formyl-tetraphenylporphyrin (21) (25 mgs, 0.039 mmol) in distilled tetrahydrofuran (15

MS LR+LSIMS (matrix: thioglycerol): Exact mass calculated for $C_{46}H_{31}F_3N_4O$ (M+1): 713.74. Found 713

$^1$H NMR (300 MHz, $CDCl_3$): δ 9.12 (1H, s, H-7), 8.84 (1H, s, H-8$^1$), 8.82–8.72 (6H, m, H-2,3,12,13, 17, 18), 8.20 (8H, m, H-5$^2$, 10$^2$, 15$^2$, 20$^2$) 7.76 (12H, m, H-5$^{3,4}$, 10$^{3,4}$, 15$^{3,4}$, 20$^{3,4}$) 2.99 (1H, br. s., —OH), -2.68 (2H, s, —NH).

$^{19}$F NMR (282 MHz, $CDCl_3$) (coupled) δ-76.87 (3F, d, —CHOH$CF_3$)

UV-VIS ($CH_2Cl_2$) $\lambda_{max}$ (rel. intensity): 420.0 (1), 450 (0.12), 517.1 (0.05), 553.0 (0.02), 596.0 (0.02), 652.0 (0.02)

Trifluoroacetyl-tetraphenylporphyrin (23)

Trifluoroacetyl-tetraphenylporphyrin (23) was synthesized according to a description of the use of tetrapropylammoniumperruthenate ($Pr_4N$)($RuO_4$) and N-methylmorpholine oxide (NMO) for oxidation of alcohols to ketones by Ley and co-workers (Griffiths, W. P.; Ley, S. V.; Whitcombe, G. P.; White, A. D. J. Chem. Soc., Chem. Commun. 1988, 1625). All flasks and syringes were flame-dried and cooled under argon. To a stirring solution of trifluoromethanol-tetraphenylporphyrin (22) (250 mgs, 0.351 mmol) in distilled methylene chloride (50 mL) was added NMO (0.46 mL, 2.24 mmol). The mixture was then left to stir at room temperature for 10 minutes, under argon, after which time a catalytic amount of TPAP (25 mgs, 0.07 mmol) was added. The reaction was monitored by TLC whereby disappearance of the dark red starting material ($R_f$=0.4) and appearance of the dark green, faster moving trifluoroacetyl-tetraphenylporphyrin ($R_f$=0.81) signaled completion of the reaction. The mixture was then washed with water (2×50 mL), the organic layer separated and dried through cotton, the solvent removed in vacuo, and the residue chromatographed on silica gel 60, 70–230 mesh, (40–60% $CH_2Cl_2$/hexanes as gradient eluent) to yield 199.3 mgs (74%) of trifluoroacetyl-tetraphenylporphyrin. One substantial impurity was visible by TLC, a purplish band ($R_f$=0.72), directly under the desired product.

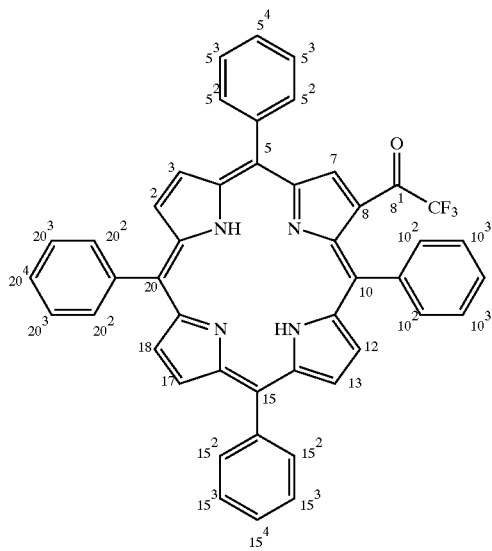

23

EA: Calculated for $C_{46}H_{29}F_3N_4O$: C, 77.73, H, 4.11; N, 7.88. Found C, 77.97; H, 4.11; N, 7.78.

MS LR+LSIMS (matrix: thioglycerol): Exact mass calculated for $C_{46}H_{29}F_3N_4O$ (M+1): 711.74. Found 711.

$^1$H NMR (300 MHz, $CDCl_3$): δ 9.25 (1H, s, H-7), 9.15-(1H, d, H-12), 9.04 (1H, d, H-3), 9.00 (2H, d, H-2,13), 8.83 (2H, s, H-17,18), 8.32 (8H, m, H-$5^2$, $10^2$, $15^2$, $20^2$), 7.81 (12H, m, H-$5^{3,4}$, $10^{3,4}$, $15^{3,4}$, $20^{3,4}$), -2.43 (2H, s, —NH).

$^{13}$C NMR (75 MHz, $CDCl_3$) (quaternary carbons are unresolved, C=29): δ 190.06, 180.53 (q, $J_{C—F}$=135 Hz), 142.10, 141.707, 141.51, 141.313, 138.15, 137.70, 136.44, 136.44, 134.82, 134.73, 134.58, 129.88, 129.39, 128.93, 128.33, 128.33, 127.94, 127.94, 127.00, 126.93, 126.88, 126.85, 122.32, 121.15, 120.61, 120.42, 118.50.

$^{19}$F NMR (282 MHz, $CDCl_3$) (coupled) δ-73.88 (3F, s, —$COCF_3$)

UV-VIS ($CH_2Cl_2$) $\lambda_{max}$ (rel. intensity) 429.0 (1), 562.0 (0.07), 562 (0.02), 606.0 (0.02), 665.0 (0.04).

Trifluoromethyl Oxime-tetraphenylporphyrin (24)

Trifluoromethyl oxime-tetraphenylporphyrin (24) was synthesized according to a modified procedure by Brunner et al. (*J. Biol. Chem.* 1980, 255, 3313–3318). All flasks and syringes were flame-dried and cooled under argon. To a stirring solution of trifluoroacetyl-tetraphenylporphyrin (23) (43 mgs, 0.06 mmol) in distilled benzene (15 mL) was added 12 mgs (0.18 mmol) of hydroxylamine hydrochloride ($NH_2OH·HCl$). Activated molecular sieves (7 Å) were also added to the 50 mL RBF. No base was added. The mixture was then left to reflux overnight. The reaction was monitored by TLC whereby disappearance of the dark green starting material (23, $R_f$=0.72) and appearance of the lighter green, slower moving trifluoromethyl oxime-tetraphenylporphyrin (24, $R_f$=0.46) signaled completion of the reaction. The mixture was then washed with water (2×50 mL), the organic layer extracted with $CH_2Cl_2$ and dried through cotton, and the solvent removed in vacuo. The crude residue was isolated to yield 26 mgs (60%) of trifluoromethyl oxime-tetraphenylporphyrin (24). One minimal impurity was visible by TLC, a light green band ($R_f$=0.24), under the desired product, but sufficient amounts could not be isolated for characterization. It should also be noted, that on standing the product (24) reverted back to its precursor (23), presumably due to hydrolysis.

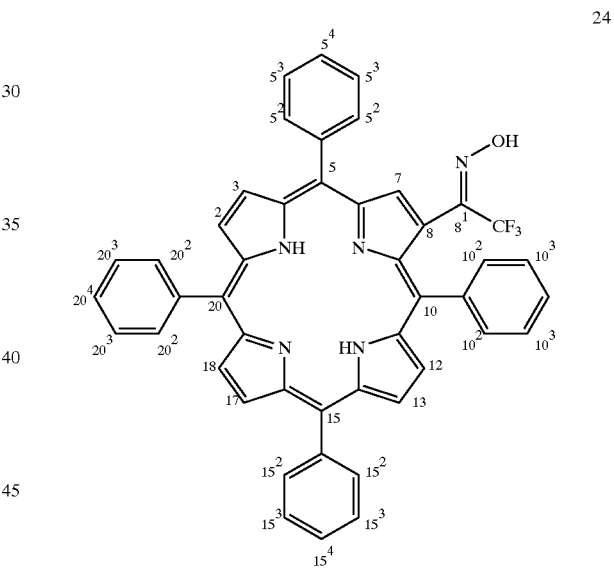

24

MS LR+LSIMS (matrix: thioglycerol): Exact mass calculated for $C_{46}H_{30}F_3N_5O$ (M+1): 725.76. Found 725.

$^1$H NMR (300 MHz, $CDCl_3$): δ 9.63 (1H, d, H-12), 8.94 (1H, s, H-7), 8.74 (1H, d, H-3), 8.73 (2H, d, H-2,13), 8.64 (2H, s, H-17,18), 8.36 (8H, m, H-$5^2$, $10^2$, $15^2$, $20^2$) 7.74 (12H, m, H-$5^{3,4}$, $10^{3,4}$, $15^{3,4}$, $20^{3,4}$) -1.70 (2H, s, —NH).

UV-VIS ($CH_2Cl_2$) $\lambda_{max}$ (rel. intensity): 435.9 (1), 539.0 (0.04), 582.1 (0.07), 618.0 (0.02), 679.0 (0.04).

EXAMPLE 10

Characterization of Compounds 8, 9 and 10

Initial characterization of compounds 8, 9, and 10 included observation as red bands by TLC (5% THF in CH$_2$Cl$_2$ eluent). All three bands were more polar than the starting material. The slowest moving band was established as the di-adduct, not only for its increased polarity (R$_{f10}$=0.09), but also because the other two bands disappeared on completion of the reaction. The mono-adduct structural isomers differed only slightly by chromatography (R$_{f8}$=0.43 and R$_{f9}$=0.33). Large scale separation was only achieved using the Chromatotron®.

The regioselectivity of the addition of the pyrazoline moiety was theoretically determined to be as shown in Scheme 1 above (via a 1,3 dipolar cycloaddition resulting in an "unsymmetrical" orientation of the pyrazoline moiety relative to the porphyrin in contrast to a symmetrical orientation wherein the two nitrogen atoms of the pyrazoline moiety are equidistant from the porphyrin macrocycle). This was experimentally confirmed as follows.

Characterization of each of the isolated protoporphyrin pyrazolines by $^1$H NMR and other methods proceeded after determination that the small amount of acid present in CDCl$_3$ (and reagent grade CH$_2$Cl$_2$) caused the degradation of these porphyrins, which are otherwise stable at room temperature. To address the structural assignment of the pyrazoline, the spectroscopic evidence of Isomer 2 is presented as exemplary. A numbered representation of a B ring pyrazoline protoporphyrin is shown below.

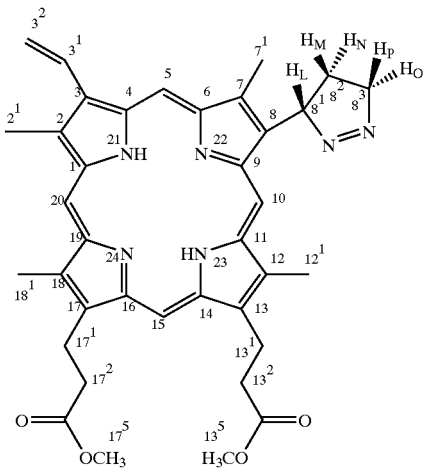

Figure 5:
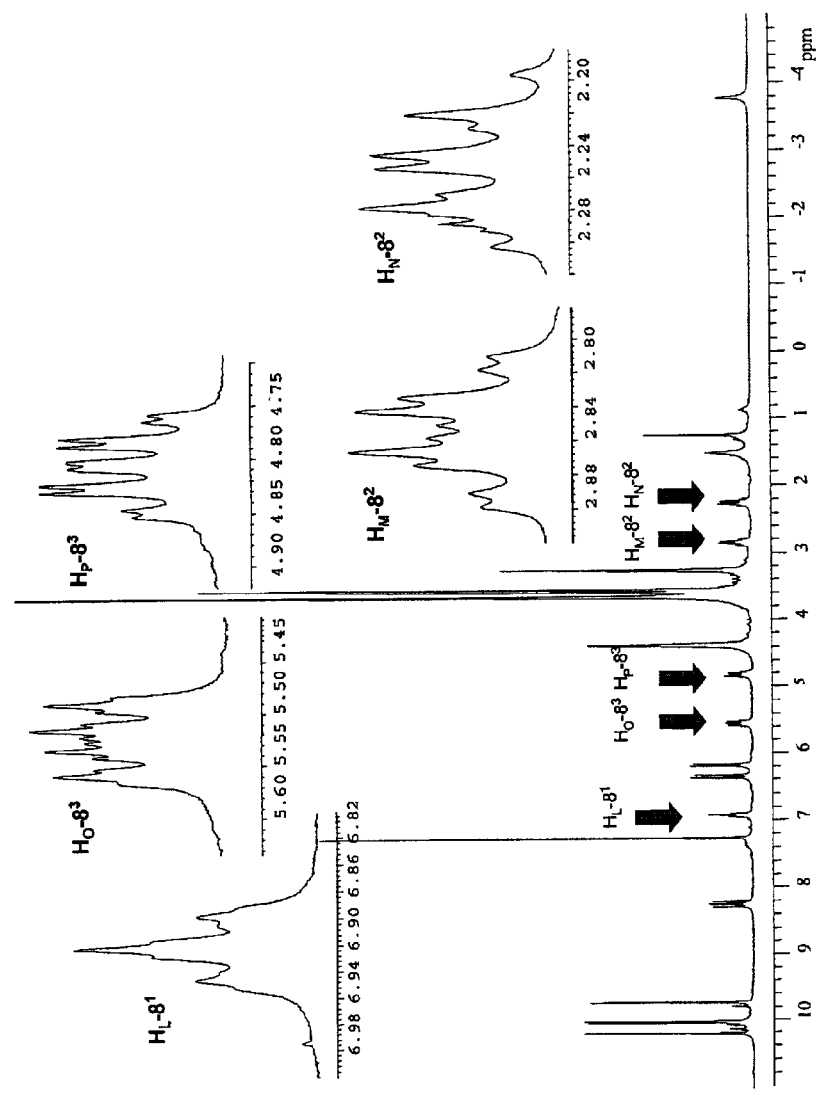
FIG. 5 shows the $^1$H NMR spectrum of pyrazoline of PP-DME (isomer 2), with expansions of pyrazoline signals.
Figure 6:
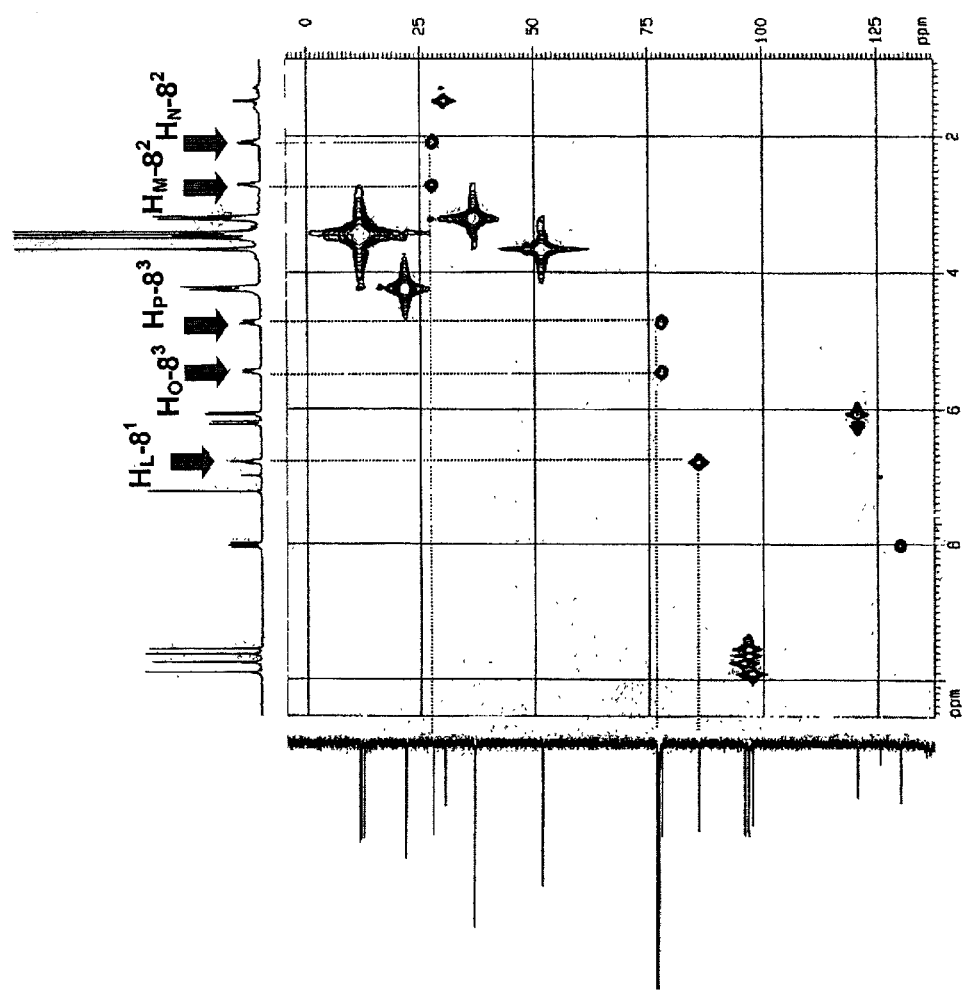
FIG. 6 shows expansion of HMQC, illustrating carbon-proton associations within pyrazoline of protoporphyrin DME.

A spectrum of the pyrazoline of protoporphyrin-DME (Isomer 2), and expansions of the pyrazoline heterocycle signals, are shown in FIG. 5. The distinctive multiplet at 6.80 ppm that integrates for a single proton can be assigned to the 'ipso' position (H$_L$-8$^1$) of the pyrazoline. The coupling pattern was difficult to decipher and was initially thought to be a triplet of triplets, indicating a symmetrical pyrazoline. If so, the splitting patterns and shifts of the four methylene proton signals were even more puzzling, and hindered rotation of the azo moiety was considered. The orientation of the pyrazoline was farther investigated using HMQC (Heteronuclear Multiple Quantum Coherence) spectra (see FIG. 6), to determine the assignment of the pairs of methylene signals to their respective carbon atoms. The results point to the unsymmetrical arrangement of the pyrazoline.

Table 4 shows the assignment of each of the primary, secondary, and tertiary carbon atoms for compound 8.

TABLE 4

HMQC Correlations for the pyrazoline of PP-DME (Isomer 2)

| Assignment H-x | $^1$H NMR (400 Mhz) δ ppm (mult., J (Hz)$^a$) | HMQC $^{13}$C Correlations (125.8 Mhz) |
|---|---|---|
| H-10 | 9.95 (s, 1H) | 97.62 |
| H-15 | 9.79 (s, 1H) | 96.86 |
| H-20 | 9.69 (s, 1H) | 96.66 |
| H-5 | 9.57 (s, 1H) | 95.89 |
| H-3$^1$ | 8.05 (m, 1H, J$_{trans}$ = 17.8, J$_{cis}$ = 11.5) | 129.99 |
| H$_L$-8$^1$ | 6.81 (m, 1H, J$_{L-M, L-N}$ = 9.8, J$_{L-O, L-P}$ 2.6) | 85.89 |
| H-3$^2$ | 6.23 (m, 1H, J$_{trans}$ = 17.8, J$_{gem}$ = 1.2) | 120.57 |
| H-3$^2$ | 6.10 (m, 1H, J$_{cis}$ = 11.5, J$_{gem}$ = 1.2) | 120.57 |
| H$_O$-8$^3$ | 5.46 (m, 1H, J$_{O-P}$ = 17.9, J$_{O-M}$ =9.8, J$_{O-N, O-L}$ = 2.6) | 77.81 |
| H$_P$-8$^3$ | 4.75 (m, 1H, J$_{P-O}$ = 17.9, J$_{P-M, P-N}$ = 9.3, J$_{P-L}$ = 2.8) | 77.81 |
| H-13$^1$ | 4.28 (t, 2H, J = 7.8) | 21.65 or 21.62 |
| H-17$^1$ | 4.24 (t, 2H, J = 7.8) | 21.65 or 21.62 |
| H-13$^5$ | 3.66 (s, 3H) | 51.69 or 51.67 |
| H-17$^5$ | 3.65 (s, 3H) | 51.69 or 51.67 |
| H-7$^1$ | 3.49 (s, 3H) | 11.42 |
| H-2$^1$ | 3.46 (s, 3H) | 12.41 |
| H-12$^1$ | 3.43 (s, 3H) | 11.83 |
| H-18$^1$ | 3.42 (s, 3H) | 11.51 |
| H-13$^2$ | 3.21 (t, 2H, J = 7.8) | 36.79 (2 × C) |
| H-17$^2$ | 3.18 (t, 2H, J = 7.8) | 36.79 (2 × C) |
| H$_M$-8$^2$ | 2.72 (m, 1H, J$_{M-N}$ = 13.0) | 27.72 |
| H$_N$-8$^2$ | 2.10 (m, 1H, J$_{M-N}$ = 13.0) | 27.72 |
| NH | −4.20 (s, 2H) | |

$^a$Only those J values that could be unambiguously assigned are recorded

COSY (1H, 1H Correlation Spectroscopy) spectra were prepared and used to reaffirm the asymmetric orientation of the pyrazoline.

To assign the respective 'A' and 'B' ring adducts, NOESY (Nuclear Overhauser Effect Spectroscopy) correlations were carried out on each of the isomers to positively identify them. With respect to the B-ring isomer, signals from the vinyl group, pyrazoline, and proprionate side chains are readily identified. Table 5 shows the NOESY correlations for the A and B-ring pyrazolines of PP-DME.

TABLE 5

| | A-Ring | | B-Ring |
|---|---|---|---|
| H-x | NOESY Correlations[b] (500 MHz) | H-x | NOESY Correlations[b] (500 MHz) |
| H-10 | Med. H-$8^2$, str. H-$8^1$, str. H-$12^1$ | H-5 | Str. H-$7^1$, w. H-$3^1$ |
| H-15 | Str. H-$13^1$, str. H-$17^1$ | H-20 | Str. H-$18^1$, str. H-$2^1$ |
| H-20 | Str. H-$18^1$, str. H-$2^1$ | H-15 | Str. H-$17^1$, str. H-$13^1$ |
| H-5 | Str. $H_L$-$3^1$, str. H-$7^1$ | H-10 | Str. $H_L$-$8^1$, str. H-$12^1$ |
| H-$8^1$ | Str. H-10, str. H-$8^2$ | H-$3^1$ | w. H-5 |
| $H_L$-$3^1$ | Str. H-$2^1$, str. H-5, str. $H_M$-$3^2$, med. $H_P$-3, w. $H_N$-$3^2$ | $H_L$-$8^1$ | Str. H-$7^1$, str. H-10, str. $H_M$-$8^2$, w. $H_P$-$8^3$, med. $H_N$-$8^2$ |
| H-$8^2$ | w. H-$7^1$, med. H-10, str. H-$8^1$ | H-$3^2$ | Str. H-$2^1$ |
| $H_O$-$3^3$ | Str. $H_P$-$3^3$, str. $H_N$-$3^2$, med. $H_M$-$3^2$ | $H_O$-$8^3$ | Str. $H_P$-$8^3$ |
| $H_P$-$3^3$ | Str. $H_O$-$3^3$, str. $H_M$-$3^2$, med. $H_L$-$3^1$ | $H_P$-$8^3$ | Str. $H_O$-$8^3$, med. $H_M$-$8^2$, w. $H_L$-$8^1$ |
| H-$13^1$ | Med. H-$12^1$, str. H-$13^2$, str. H-15 | H-$13^1$ | Med. H-$12^1$, str. H-$13^2$, str. H-15 |
| H-$17^1$ | Str. H-15, str. H-$17^2$, med. H-$18^1$ | H-$17^1$ | Str. H-15, str. H-$17^2$, med. H-$18^1$ |
| H-$7^1$ | Str. H-5, w. H-$8^2$ | H-$12^1$ | Str. H-10, med. H-$13^1$ |
| H-$2^1$ | Str. $H_L$-$3^1$, str. H-20 | H-$18^1$ | Str. H-20, med. H-$17^1$ |
| H-$12^1$ | Str. H-10, med. H-$13^1$ | H-$7^1$ | Str. H-5, str. $H_L$-$8^1$ |
| H-$18^1$ | med. H-$17^1$, med H-$17^2$, str. H-20 | H-$2^1$ | str. H-$3^2$, str. H-20 |
| H-$13^2$ | str. H-$13^1$ | H-$13^2$ | Str. H-$13^1$ |
| H-$17^2$ | str. H-$17^1$ | H-$17^2$ | Str. H-$17^1$ |
| $H_M$-$3^2$ | str. $H_N$-$3^2$, str. $H_L$-$3^1$, str. $H_P$-$3^3$, med. $H_O$$3^3$ | $H_M$-$8^2$ | Str. $H_N$-$8^2$, str. $H_L$-$8^1$, med. $H_P$-$8^3$ |
| $H_N$-$3^2$ | str. $H_M$-$3^2$, str. $H_O$-$3^3$, w. $H_L$-$3^1$ | $H_N$-$8^2$ | str. $H_M$-$8^2$, med. $H_L$-$8^1$ | str. = strong, med. = medium, w. = weak

Thus the two structural isomers, undistinguishable by mass spectrometry, UV-vis spectroscopy, $^{13}$C NMR, $^1$H NMR, and barely separable by chromatography were assigned their respective conformations using 2D NMR spectroscopy. The faster moving 'Isomer 1' ($R_f$=0.43) is the A-ring adduct, and the slower Isomer 2 is thus confirmed as the B-ring isomer. This conclusion is supported by the crystal structure of the photoproduct of the A-ring pyrazoline of protoporphyrin-DME.

The di-adduct pyrazoline of protoporphyrin-DME (10) did not present the isolation challenges of the A and B-ring adducts. It was much more polar than either of the mono-adducts, thus distinguishable by TLC, as well as by MS and UV. The extensive 2D NMR experiments to assign the regiochemistry of the single adducts were extrapolated to similarly assign those of the di-adduct pyrazolines. Comparisons of the proton NMR of the starting material, protoporphryin-DME, and the di-adduct pyrazoline product indicated the presence of more than one porphyrin in solution in the latter case. This follows because in the di-adduct, two stereocenters are created at each of the pyrazolines, and the result is a pair of diastereomers. The comparison also confirmed the complete disappearance of the vinyl signals for the di-adduct. This is in contrast to the A and B-ring adducts, which had residual vinyl signals.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A photosensitizer compound represented by one of the following formulas

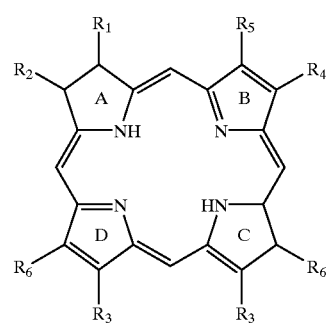

1A

-continued

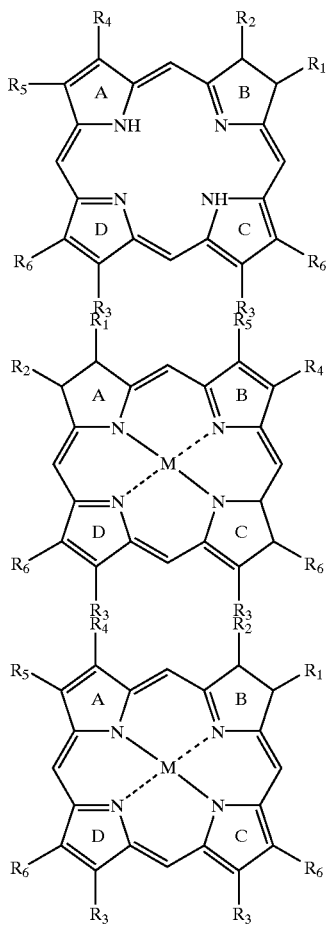

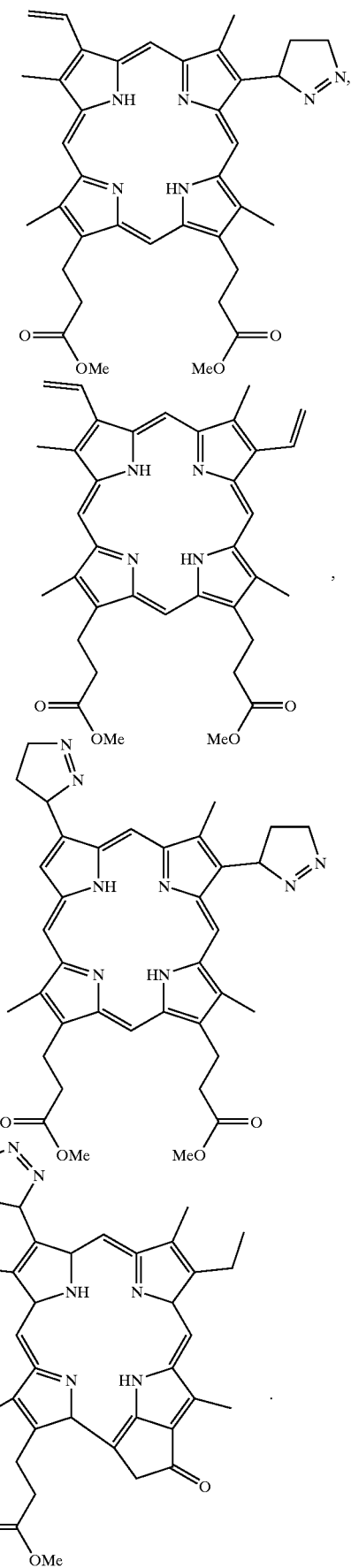

wherein one, or both, of $R_1$ and $R_4$ has, or have, the structure of

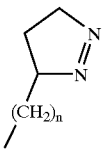

wherein n is an integer from 0 to 6 wherein M is a metal selected from Co, Ni(II), Cu(II), Zn(II), Fe(III), Sn, Ge, Si, Ga, Al, Mn(III), Gd(III), In and Tc;

$R_2$, $R_5$ and $R_6$ are independently hydrogen, a lower alkyl group; a lower alkyl carboxylic acid or a salt, amide, ester or acylhydrazone thereof; a carboxylic acid ester (or carbalkoxy) group (2–6C); hydroxy; nitro; amino; sulfonyl; or —CONR$_7$CO— where $R_7$ is aryl (6–10C); or alkyl (1–6C); and each $R_3$ is independently
hydrogen; hydroxy; a lower alkyl carboxylic acid or a salt, amide, ester or acylhydrazone thereof; nitro; amino; a carboxylic acid ester (or carbalkoxy) group (2–6C); sulfonyl; or aryl (6–10C).

2. A method to conduct PDT comprising contacting a target substrate with a photosensitizing compound according to claim 1; and irradiating said substrate with light containing a wavelength which activates said compound.

3. The method of claim 2 wherein said light also crosslinks said compound to said target substrate.

4. The method of claim 2 further comprising repeat irradiation of the substrate with light absorbed by the compound.

5. A photosensitizer compound represented by one of the following formulas

6. A method to conduct PDT comprising contacting a target substrate with a photosensitizing compound according to claim 5; and irradiating said substrate with light containing a wavelength which activates said compound.

7. The method of claim 6 wherein said light also crosslinks said compound to said target substrate.

8. The method of claim 6, further comprising repeat irradiation of the substrate with light absorbed by the compound.

* * * * *